US007769606B2

(12) United States Patent
Boone et al.

(10) Patent No.: US 7,769,606 B2
(45) Date of Patent: Aug. 3, 2010

(54) INTERACTIVE HEALTH INSURANCE SYSTEM

(76) Inventors: H. Keith Boone, 3333 Bagley Passage, Duluth, GA (US) 30097; Cecil R. Dearborne, 642 W. Cornelia St. 3N, Chicago, IL (US) 60657; Brian S. Kaplan, 1662 Clay St., San Francisco, CA (US) 94109; Laurie H. Maiser, 15645 25th Pl. N. Unit E, Plymouth, MN (US) 55447; David D. Montgomery, 4E 65th St., Apt. 4 1/2, New York, NY (US) 10021; Gayle Y. Popp, 22 Walt Whitman Tr., Morristown, NJ (US) 07960; Glenn A. Stolar, 6395 Oxbow Bend, Chanhassen, MN (US) 55317; Deborah L. Worrell, 1655 Canyon Run, Naperville, IL (US) 60565; Jim D. Emery, 1515 E. Franklin, Unit 35, Chapel Hill, NC (US) 27514; Stuart R. Friedman, 1235 W. George, #110, Chicago, IL (US) 60657; Melissa H Nuttall, 1642 W. Pierce, Chicago, IL (US) 60622; Praveen G. Thadani, 105 Flamingo Dr., Roselle, IL (US) 60172; Nada M. Hakimi, 1849 W. North Ave. #11, Chicago, IL (US) 60622; Katherine B. Hatting, 515 Daventry Rd., Berwyn, PA (US) 19312; William P. Whitely, 2657 Woodbridge Rd., Wayzata, MN (US) 55391; David A. Rey, 15 Windsong Way, Lafayette, CA (US) 94549; Robert S. Frisch, 31 Farlow Rd., Newton, MA (US) 02458; Brian A. Johnson, 888 Tower Rd., Winnetka, IL (US) 60093

( * ) Notice: Subject to any disclaimer, the term of this patent is extended or adjusted under 35 U.S.C. 154(b) by 1626 days.

(21) Appl. No.: 10/187,424

(22) Filed: Jul. 1, 2002

(65) Prior Publication Data
US 2004/0002924 A1 Jan. 1, 2004

(51) Int. Cl.
*A06Q 40/00* (2006.01)
(52) U.S. Cl. .............. 705/4; 705/2; 705/3; 705/28; 705/32; 705/40; 709/204; 707/104
(58) Field of Classification Search ............... 705/2, 705/3, 4, 36 R; 709/204; 379/221.02; 707/104.1; 380/270
See application file for complete search history.

(56) References Cited

U.S. PATENT DOCUMENTS 4,491,725 A * 1/1985 Pritchard .................. 705/2
5,930,759 A * 7/1999 Moore et al. ............... 705/2

(Continued)

OTHER PUBLICATIONS

Consumers Union; Choosing a health plan-Tip sheet 2001; www.consumersunion.org.*
www.wikipedia.com; description of preferred provider organization.*
Dialog search history.*
Dialog search results.*

*Primary Examiner*—Luke Gilligan
*Assistant Examiner*—Dilek B Cobanoglu
(74) *Attorney, Agent, or Firm*—Kinney & Lange, P.A.

(57) ABSTRACT

A method for administrating healthcare services allows providers to select cost-sharing levels for each service. Cost-share selections and other provider practice characteristics are stored in a dynamic, cost-sharing database. Individuals seeking a provider can access the database through a network and perform a provider search based on selected criteria. Individuals that receive services from a provider pay the appropriate cost-share at the time of service, and an administrator pays an additional amount based on a fee schedule specifying the amount the administrator will pay for the specified service.

30 Claims, 27 Drawing Sheets

U.S. PATENT DOCUMENTS

| | | | |
|---|---|---|---|
| 6,006,191 A * | 12/1999 | DiRienzo | 705/2 |
| 6,581,067 B1 * | 6/2003 | Bjergo et al. | 707/104.1 |
| 6,735,569 B1 * | 5/2004 | Wizig | 705/4 |
| 2002/0055974 A1 * | 5/2002 | Hawkes et al. | 709/204 |
| 2002/0094074 A1 * | 7/2002 | Lurie | 379/221.02 |
| 2002/0123907 A1 * | 9/2002 | Strayer | 705/2 |

* cited by examiner

| CPT Code | Procedure Description | Medicare Rate | UHC Percent Contribution | UHC Contribution | Total Reimbursement $70 | Total Reimbursement $150 | Total Reimbursement $275 | Total Reimbursement as Percent Medicare $70 | Total Reimbursement as Percent Medicare $150 | Total Reimbursement as Percent Medicare $275 |
|---|---|---|---|---|---|---|---|---|---|---|
| 95810 | Polysomnography, 4 or more | $668.18 | 80% | $534.55 | $604.55 | $684.55 | $809.55 | 90% | 102% | 121% |
| 95810 | Polysomnography, 4 or more | $215.64 | 70% | $150.95 | $220.95 | $300.95 | $425.95 | 102% | 140% | 198% |
| 95951 | EEG monitoring/videorecord | $321.36 | 70% | $224.95 | $294.95 | $374.95 | $499.95 | 92% | 117% | 156% |
| 95810 | Polysomnography, 4 or more | $452.54 | 70% | $316.78 | $386.78 | $466.78 | $591.78 | 85% | 103% | 131% |
| 95951 | EEG monitoring/videorecord | $902.04 | 85% | $766.73 | $836.73 | $916.73 | $1,041.73 | 93% | 102% | 115% |
| 95808 | Polysomnography, 1-3 | $495.22 | 70% | $346.66 | $416.66 | $496.66 | $621.66 | 84% | 100% | 126% |
| 95807 | Sleep study, attended | $399.75 | 70% | $279.82 | $349.82 | $429.82 | $554.82 | 88% | 108% | 139% |
| 95805 | Multiple sleep latency test | $390.76 | 70% | $273.53 | $343.53 | $423.53 | $548.53 | 88% | 108% | 140% |
| 95811 | Polysomnography w/cpap | $694.71 | 80% | $555.77 | $625.77 | $705.77 | $830.77 | 90% | 102% | 120% |
| 95811 | Polysomnography w/cpap | $231.19 | 70% | $161.84 | $231.84 | $311.84 | $436.84 | 100% | 135% | 189% |
| 95553 | EEG monitoring/computer | $454.52 | 70% | $318.16 | $388.16 | $468.16 | $593.16 | 85% | 103% | 131% |
| 95950 | Ambulatory eeg monitoring | $313.91 | 70% | $219.73 | $269.73 | $369.73 | $494.73 | 92% | 118% | 158% |
| 95808 | Polysomnography, 1-3 | $176.13 | 70% | $123.29 | $193.29 | $273.29 | $398.29 | 110% | 155% | 226% |
| 95953 | EEG monitoring/computer | $280.27 | 70% | $196.19 | $266.19 | $346.19 | $471.19 | 95% | 124% | 168% |
| 95957 | EEG digital analysis | $184.80 | 70% | $129.36 | $199.36 | $279.36 | $404.36 | 108% | 151% | 219% |
| 95864 | Muscle test, 4 limbs | $213.46 | 70% | $149.42 | $219.42 | $299.42 | $424.42 | 103% | 140% | 199% |
| 95956 | Eeg monitoring, cable/radio | $180.62 | 70% | $126.43 | $196.43 | $276.43 | $401.43 | 109% | 153% | 222% |
| 95811 | Polysomnography w/cpap | $463.52 | 70% | $324.46 | $394.46 | $474.46 | $599.46 | 85% | 102% | 129% |
| 95813 | Electroencephalogram (EEG) | $205.63 | 70% | $143.94 | $213.94 | $293.94 | $418.94 | 104% | 143% | 204% |
| 95808 | Polysomnography, 1-3 | $319.09 | 70% | $223.36 | $293.36 | $373.36 | $498.36 | 92% | 117% | 156% |
| 95920 | Intraop nerve test add-on | $191.02 | 70% | $133.71 | $203.71 | $283.71 | $408.71 | 107% | 149% | 214% |
| 95951 | EEG monitoring/videorecord | $580.68 | 75% | $435.51 | $505.51 | $585.51 | $710.51 | 87% | 101% | 122% |
| 95958 | EEG monitoring/function test | $272.11 | 70% | $190.47 | $260.47 | $340.47 | $465.47 | 96% | 125% | 171% |
| 95829 | Surgery electrocorticogram | $305.35 | 70% | $213.75 | $283.75 | $363.75 | $488.75 | 93% | 119% | 160% |
| 95961 | Electrode stimulation, brain | $175.06 | 70% | $122.54 | $192.54 | $272.54 | $397.54 | 110% | 156% | 227% |
| 95829 | Surgery electrocorticogram | $394.23 | 70% | $275.96 | $345.96 | $425.96 | $550.96 | 88% | 108% | 140% |
| 95805 | Multiple sleep latency test | $291.25 | 70% | $203.87 | $273.87 | $353.87 | $478.87 | 94% | 122% | 164% |
| 95956 | Eeg monitoring, cable/radio | $792.72 | 85% | $673.81 | $743.81 | $823.81 | $948.81 | 94% | 104% | 120% |
| 95961 | Electrode stimulation, brain | $231.76 | 70% | $162.24 | $232.24 | $312.24 | $437.24 | 100% | 135% | 189% |
| 95958 | EEG monitoring/function test | $349.83 | 70% | $244.88 | $314.88 | $394.88 | $519.88 | 90% | 113% | 149% |
| 95962 | Electrode stim, brain add-on | $243.22 | 70% | $170.26 | $240.26 | $320.26 | $445.26 | 99% | 132% | 183% |
| 95806 | Sleep study, unattended | $269.88 | 70% | $188.92 | $258.92 | $338.92 | $463.92 | 96% | 126% | 172% |
| 95954 | EEG monitoring/giving drugs | $222.52 | 70% | $155.77 | $225.77 | $305.77 | $430.77 | 101% | 137% | 194% |
| 95807 | Sleep study, attended | $284.04 | 70% | $198.83 | $268.83 | $348.83 | $473.83 | 95% | 123% | 167% |
| 95962 | Electrode stim, brain add-on | $186.52 | 70% | $130.57 | $200.57 | $280.57 | $405.57 | 108% | 150% | 217% |
| 95950 | Ambulatory eeg monitoring | $214.54 | 70% | $150.18 | $220.18 | $300.18 | $425.18 | 103% | 140% | 198% |
| FAMILY COPAYMENTS AND REIMBURSEMENT | | | | | $70 | $150 | $275 | 95% | 118% | 155% |

*Fig. 1a*

*Welcome to* My Universe                                   UnitedHealthcare®

| Home | Contact UHC | About Us | Glossary | FAQ's | Site Map |

○ Research My Care

| Knee Replacement Treatment Budget |

Here are the elements of your care that are typically required for a knee replacement. Click on one to see the providers available to you, or select your favorite.

168 ─

| Orthopedic Surgeons | Dr. Susan Riley is your favorite Orthopedic Surgeon | Change or Select One [Select One] |
| Surgical Facilities | No favorite Surgical Facility Selected. | Select One |
| Rehabilitation Facilities | No favorite Rehabilitation Facility Selected | Select One |
| Personal Trainers | No favorite Personal Trainer Selected | |

My Profile

My Healthcare
● Research My Care
  - My Out-of-Pockets
  - My Section 125
  - My Pharmacy
  - My Health Goals
  - My Health Diary My Health Library My Feedback Contact UHC

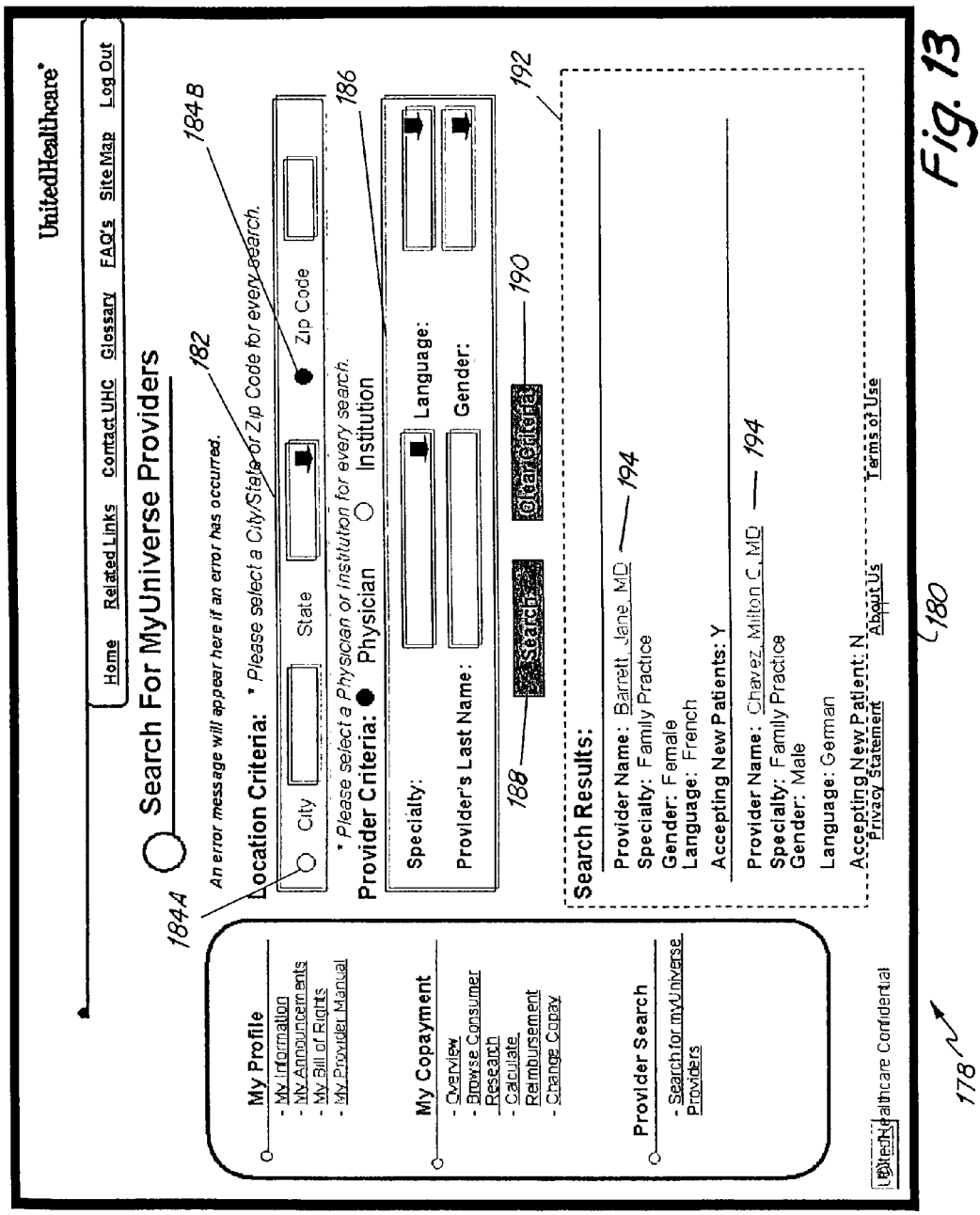

Welcome to myUniverse

Home | Related Links | Contact UHC | Glossary | FAQ's | Site Map | Log Out

UnitedHealthcare®

Physician Profile - Dr. Jane Barrett

Return to CSR Home Page

| | | |
|---|---|---|
| SPECIALTY: | Orthopedic Surgery | Username: JBarrett |
| BIRTHDATE: | 1/4/62 | Seen by CSR only |
| ACCEPTING NEW PATIENTS: | Yes | |
| HOMEPAGE: | www.barrett.com | |
| EMAIL: | barrettjane@hotmail.com | |
| GENDER: | Female | |
| LOCATION: | 1800 N. Westwood Blvd | |
| | Suite 700 | |
| | Century City, CA 90210 | |
| OFFICE PHONE NUMBER: | (310) 589 - 2300 | |
| HOURS: | Mon | none |
| | Tues | 8AM-Noon |
| | Wed/es | 8AM-Noon |
| | Thurs | 1PM-4PM |
| | Fri | 1PM-4PM |
| | Sat | 1PM-4PM |
| | Sun | none |
| WEB CONSULTATION: | N | |
| LOCATION: | 161 N 10th Street | |
| | Century City, CA 90210 | |
| OFFICE PHONE NUMBER: | (310) 568 - 1000 | |
| PAYMENT OPTION(S): | American Express | |
| | Cash | |
| COPAY: | Office Visit | $25 |
| | X-Ray | $30 |
| LANGUAGE(S) SPOKEN: | French | |
| AFFILIATIONS: | Stanford Hospital | |
| | Daniel Freeman Memorial Hospital | |

Announcements
- My copayment has changed to $50.
- I am happy to announce that I am back from maternity leave after having a baby boy, named Cole. I will be accepting new patients.
- New Patients will not be required to pay the $50 copayment on their first visit.

[Add To Treatment Budget] — 200

[Add To Favorite Physicians]

*These buttons are available ONLY for members!* — 202

My Profile
- My Information
- My Announcements
- My Bill of Rights
- My Provider Manual

My Copayment
- Overview
- Browse Consumer Research
- Calculate Reimbursement
- Change Copay

Provider Search
- Search for myUniverse Providers

198

196

Privacy Statement | About Us | Terms of Use

UnitedHealthcare Confidential

*Fig. 14*

Welcome to myUniverse

| Home | Related Links | Contact UHC | Glossary | FAQ's | Site Map | Log Out |

○ myCopayment - Submit Copay

Instructions to submit copay:

Lorem ipsum dolor sit amet, consec tetuer adipiscing elit.
Lorem ipsum dolor sit amet, consec tetuer adipiscing elit.
Lorem ipsum dolor sit amet, consec tetuer adipiscing elit.

Specialty: [cosmetic surgeon ▶] ~296

Effective Date: [6/1/01 to 12/31/01 ▶] ~298

~294

| Copay Group | Current Copay | Select Copay |
|---|---|---|
| Office Visit: | $50 | [$25 ▶] |
| Lab: | N/A | [$25 ▶] |
| X-Ray: | $30 | [$25 ▶] |

~302  ~304  ~306

~300

[Submit] ~308    [Cancel] ~310

- myInformation
  - Profile
  - Announcements
  - Bill of Rights
  - Provider Manual

- myCopayment
  - Overview
  - Browse Consumer Research
  - Reimbursement Scenarios
  - Submit Copay

- Provider Search
  - Search for myUniverse providers

INTERACTIVE HEALTH INSURANCE SYSTEM

BACKGROUND OF THE INVENTION

This invention relates generally to a method of using a database through a network such as the Internet, interactive voice response system, or other data networks. In particular, the present invention is concerned with a method of designing benefits and managing healthcare reimbursements based on information stored in a database.

Health plans have traditionally been in the business of collecting premiums from employers, unions, the government, individuals, or other customers and arranging for members covered by the premium to receive services from hospitals, physicians, or other healthcare providers. The plan subsequently reimburses the providers for services they performed.

It is common for members to share in the cost of these services by paying either copayments or coinsurance (cost-sharing) to providers, which the health plans negotiate with customers. The amount may vary between services, but not between members or providers. Therefore, different members going to different providers for the same service will pay identical cost-sharing. Effectively, there are no economic forces at play in the member's choice of provider.

Health plans also negotiate reimbursements with providers. Reimbursements may vary between services. For example, surgeries may be paid at a higher rate than office visits. Reimbursements may also vary between products. For example, providers belonging to a preferred provider option may be reimbursed differently for the same service furnished by a provider belonging to a health maintenance organization. In addition, reimbursement may vary by provider. For example, popular providers may be paid more than less popular providers, or providers with geographic exclusivity may be paid more than those who have many competitors. Members pay the same cost-share regardless of which provider they choose. Since there is no difference in cost from the member's perspective, normal market economics are not at play. This system has prevented providers from differentiating themselves from other providers and marketing their skills to consumers.

The healthcare industry in the United States stands at a cross roads between a government-driven and a market-driven approach. While proponents of the government-driven model advocate consumer rights, further government regulation will ultimately be detrimental to the consumer. Therefore, there needs to be a lead in a move toward the market-driven approach. This invention will facilitate the market-driven approach.

BRIEF SUMMARY OF THE INVENTION

The invention is a method and technology for administering and determining reimbursements to providers of services. The method involves maintaining a dynamic database that stores practice characteristics and provider-selected cost-sharing levels (which individuals that receive the services must pay to the providers). Individuals can search this database to find providers that offer desired practice characteristics at various cost-sharing levels.

BRIEF DESCRIPTION OF THE DRAWINGS

FIG. 1a is a table listing sample cost-share levels and reimbursements calculated and stored in the dynamic cost-sharing database.

FIG. 11 is a sample screen which automatically lists elements of care required for a selected treatment budget.

FIG. 13 is a sample screen used to conduct a search for a provider.

FIG. 14 is a sample screen showing a provider profile.

FIG. 24 is a sample screen illustrating steps in submitting and changing copayment levels.

DETAILED DESCRIPTION

Figure 1:
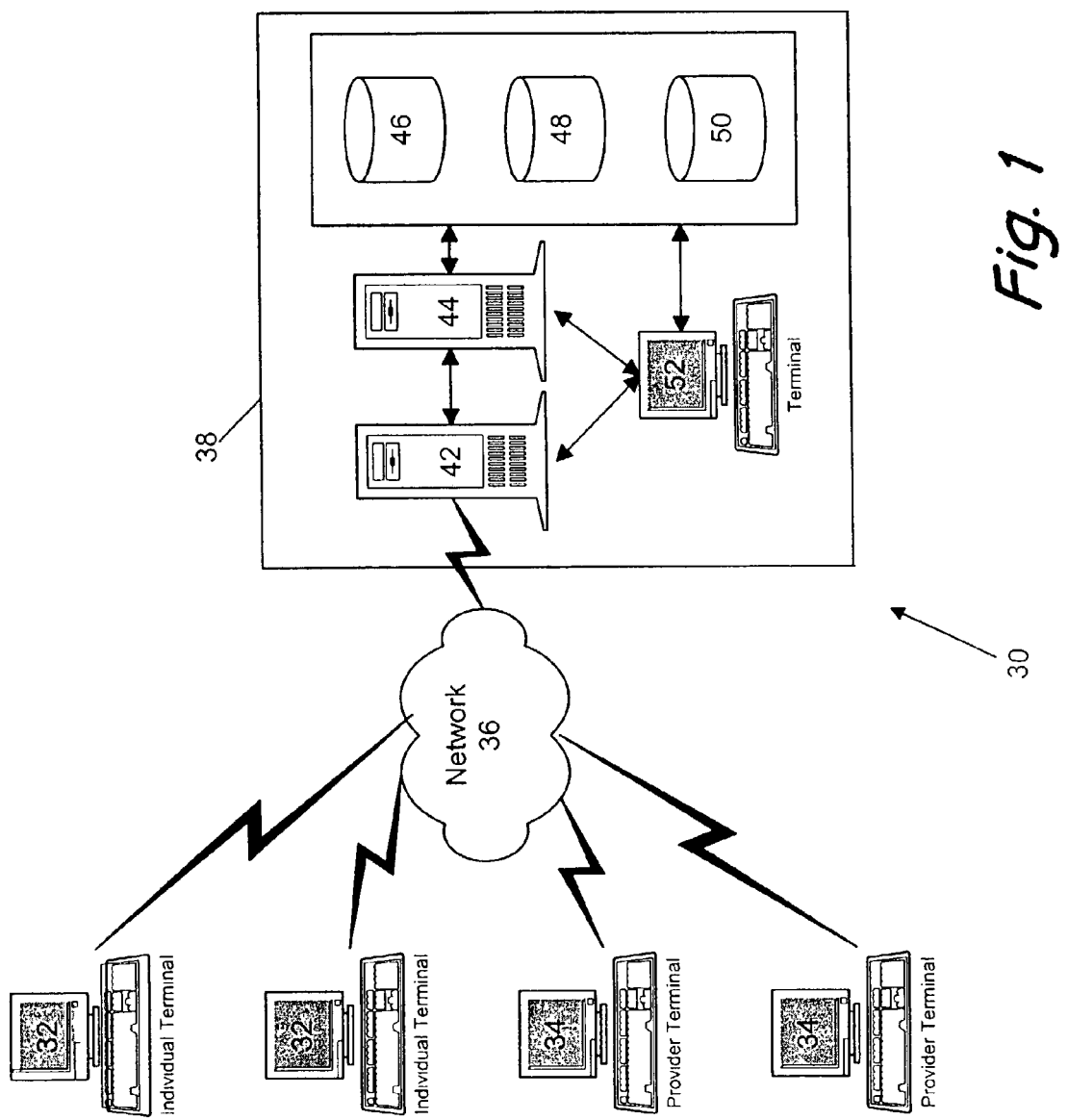
FIG. 1 is a schematic view of the preferred embodiment of the Service Administering System.

FIG. 1 is a schematic representation of Service Administering System 30. System 30 includes one or more Individual terminals 32, one or more Provider terminals 34, Network 36, and Computer system 38. Computer system 38 includes Network server 42, Application server(s) 44, Provider Information database 46, Individual Information database 48, Administrator Information database 50, and Terminal 52.

Communication links connect the components of System 30. Individual terminals 32 and Provider terminals 34 are linked to Network 36 which, in turn, is linked to Computer system 38. Network server 42 links Network 36 to Computer system 38. Network server 42 is also linked to Application server(s) 44 and Terminal 52. Application server(s) 44 is then linked to databases 46, 48, and 50 and Terminal 52. Databases 46, 48, and 50 are also linked to Terminal 52.

In operation, users access System 30 through terminals 32 and 34 and Network 36, which may be the Internet or any other type of data network. Computer system 38 provides the means for an administrator to run and manage System 30 and allow users to access information and use various programs, which will be discussed shortly, over Network 36. Computer system 38 may be a network itself, or it may be contained within one computer.

Network server 42 provides software to allow access between Network 36 and Computer system 38. Application server(s) 44 contains programs that run System 30 and perform user functions. Information entered by users and the administrator is stored in databases 46, 48, and 50. Terminal 52 interfaces with all components of Computer system 38 to allow the administrator to maintain System 30 and update the information it contains.

Provider Information database 46 contains practice characteristics of providers. These include specialties, practice locations, telephone numbers, hours, average "wait" time at the provider's office, openings at specific days and times, which hospitals a physician provider admits patients to, patient satisfaction, general personal information, credentials, affiliations, languages spoken, gender, provider-selected cost-sharing levels, etc. Database 46 also stores contracts with the administrator, announcements intended to be read by other users, reimbursement scenarios (discussed below), money account information, etc.

Individual Information database 48 contains general personal information, favorite providers of the individual and individual's family, eligibility and benefits, treatment budgets, tracked out-of-pocket expenses, money account information, etc.

Administrator Information database 50 includes fee schedules and maintains information for individual cost-sharing per single transaction in a novel fashion. Provider specialty-specific utilization profiles are developed based on the administrator's provider specialty definitions and the frequency of service of each of these defined services (for example, CPT Codes) at a market-driven specific industry standard level. First, each specialty utilization profile is divided into copayment families. In the preferred embodiment, the number of copayment families applies to each category of service. In this example, three copayment families are formed and include office visits, office-based procedures, and facility-based procedures. These copayment families can further be divided into major and minor procedures. Preferably, office-based procedures and facility-based procedures are divided by major and minor procedures. Next, to calculate initial cost-sharing levels, a utilization-weighted reimbursement factor is created for procedures within each copayment family. The reimbursement factors for each copayment family are added and used to generate a total copayment family weight which is then used to create a normalized weight for each procedure within each copayment family. This normalized weighting indicates the percentage that each procedure performed by an average provider in that specialty contributes to the total copayment family reimbursement. Next, the amount that the administrator reimburses the provider for each procedure and the target range of total reimbursement to the provider are determined and used to calculate corresponding cost-sharing levels for each procedure.

Preferably, the administrator reimburses the provider on a fee schedule which is based on a market-driven specific industry standard. This level of reimbursement allows for reasonable cost-sharing. The target range of total reimbursement to providers falls into three tiers. The middle tier is based on the market average, and the low and high tiers are based on the market spread. The low cost-sharing level reimburses the provider below the market average on an aggregate basis, while the high cost-sharing level allows the providers to make more money than they currently make on an aggregate basis. FIG. 1a illustrates an example of using this process.

FIG. 1a shows a table listing examples of procedures, or services, from a copayment family and corresponding examples of administrator contributions for Neurology major procedures in a facility. Column one lists CPT codes for the procedures listed in column two. Column three is the Medicare rate, which is an example of a market-driven specific industry standard. Column four is the percentage of the standard that the administrator reimburses the providers for the particular procedure. Column five is the dollar amount of reimbursement for each procedure to the provider by the administrator. This is also referred to as the fee schedule. Columns six, seven, and eight list the total reimbursement to the providers using either the low, middle, or high cost-sharing levels, respectively. Columns nine, ten, and eleven list the total reimbursements as a percent of Medicare reimbursement that the provider would receive using either the low, middle, or high cost-sharing levels, respectively.

The Medicare rate is listed for each procedure within the copayment family. The first procedure listed is a "polysomnography, 4 or more", having CPT code 95810, with a specific industry standard rate of $668.18. The percentage of the standard that the administrator has determined to reimburse for this procedure in this example is 80%, which gives a reimbursement amount of $534.55. The total reimbursement to the provider is calculated using three cost-sharing levels which are determined using the method described above. For this copayment family, the three levels are $70, $150, and $275. Adding these cost-shares to the administrator's reimbursement gives total reimbursements of $604.55 for the low level, $684.55 for the middle level, and $809.55 for the high level. The total reimbursements are then shown as a percentage of the market-driven specific industry standard which is the Medicare rate in this instance. For this example, the low level cost-share reimburses the provider 90% of the standard. The middle and high level cost-shares reimburse the provider 102% and 121% of the standard, respectively.

The average of each level of total reimbursement percentage for the copayment family is shown at the bottom of columns nine, ten, and eleven. As seen in this example, the low level reimburses about 95% of the standard, the middle level reimburses about 118% of the standard, and the high level reimburses about 155% of the standard.

The initial cost-sharing levels are evaluated for the following: (1) the implications on provider reimbursement for each procedure and the overall anticipated reimbursement using the copayment family cost-sharing level and (2) the variation based on the expected number of actual cost-shares collected (i.e. determining how cost-sharing collections will be counted when, for example, a procedure includes one or more office consults or when multiple diagnostic tests are performed during the same office visit). Revisions may be made to copayment family categories, to fee schedules for procedures, to cost-sharing levels, by creating exceptions, etc.

Administrator information database 50 makes up a dynamic cost-sharing database, which is a very novel feature of System 30. Appropriate security measures are taken to ensure that all information stored in the databases is kept confidential.

In the preferred embodiment of the invention, Network 36 is the Internet, and System 30 is used for administering delivery of healthcare to members of a healthcare plan. System 30 may optionally be used as an auction of services in an insured environment. Users of System 30 enter information through either healthcare administrator, provider, or individual computer terminals. Therefore, the description that follows will be in this context.

Figure 2:
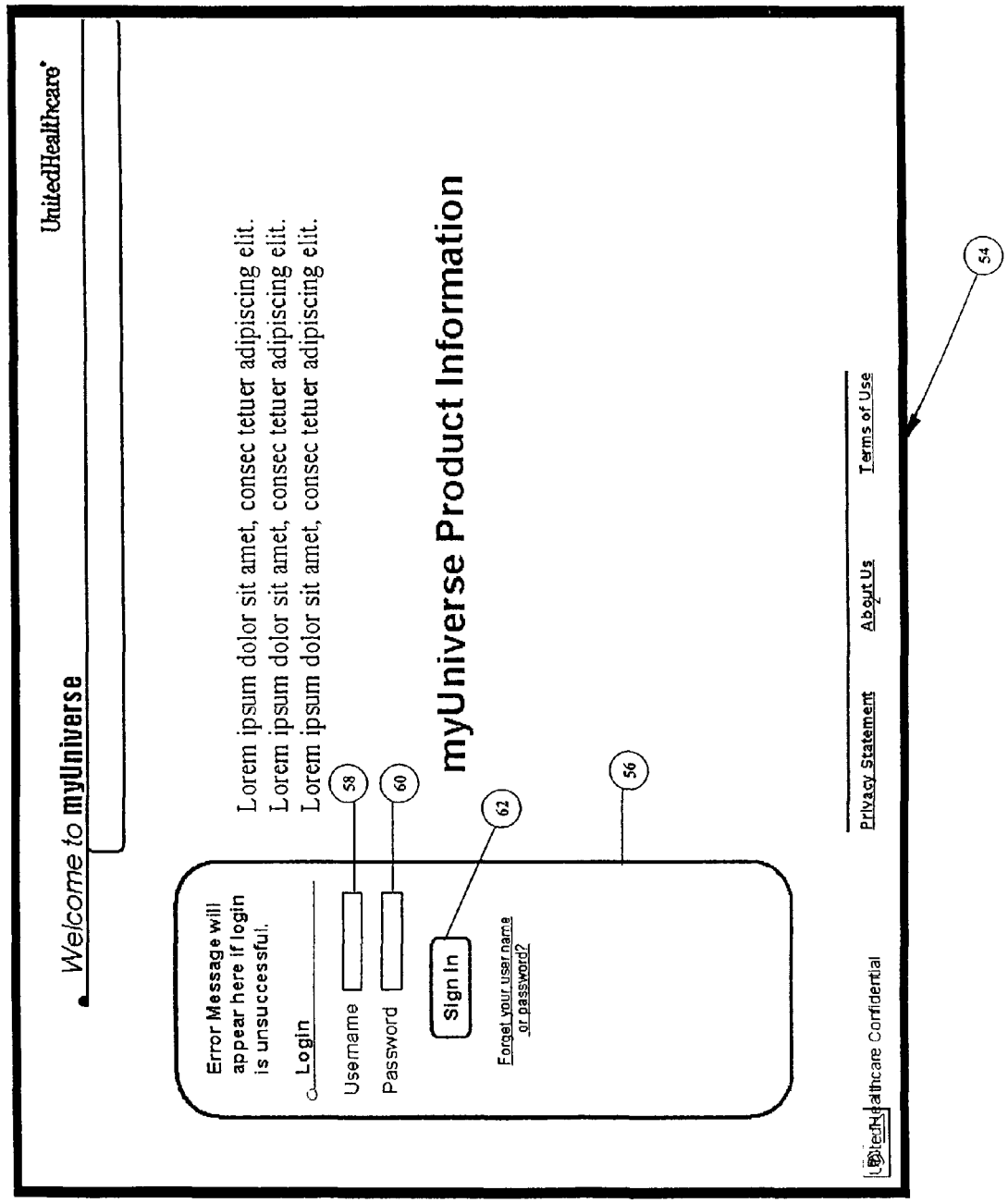
FIG. 2 is a sample screen of the System's home page.

In System 30 of the present invention, a user will open up System 30 web site using the Internet. FIG. 2 shows System home page 54, which includes Navigation bar 56 with Username field 58, Password field 60, and Sign In button 62. Navigation bar 56 is used throughout this embodiment of System 30, but its main topics may vary from screen to screen and depend on whether the user is a member or a provider. A "member" refers to anyone seeking a provider for services, and "providers" include facilities and institutions as well as persons providing services. The user, either a member or provider, logs in onto System 30 by entering a username into Username field 58 and a password into Password field 60 and clicking Sign In button 62. Usernames and passwords are previously given to users. System 30 will provide options for users to change passwords or retype it if the user did not enter it correctly. Preferably, there is also an option that allows the user to retrieve hints if he/she forgets his/her username or password.

Figure 3:
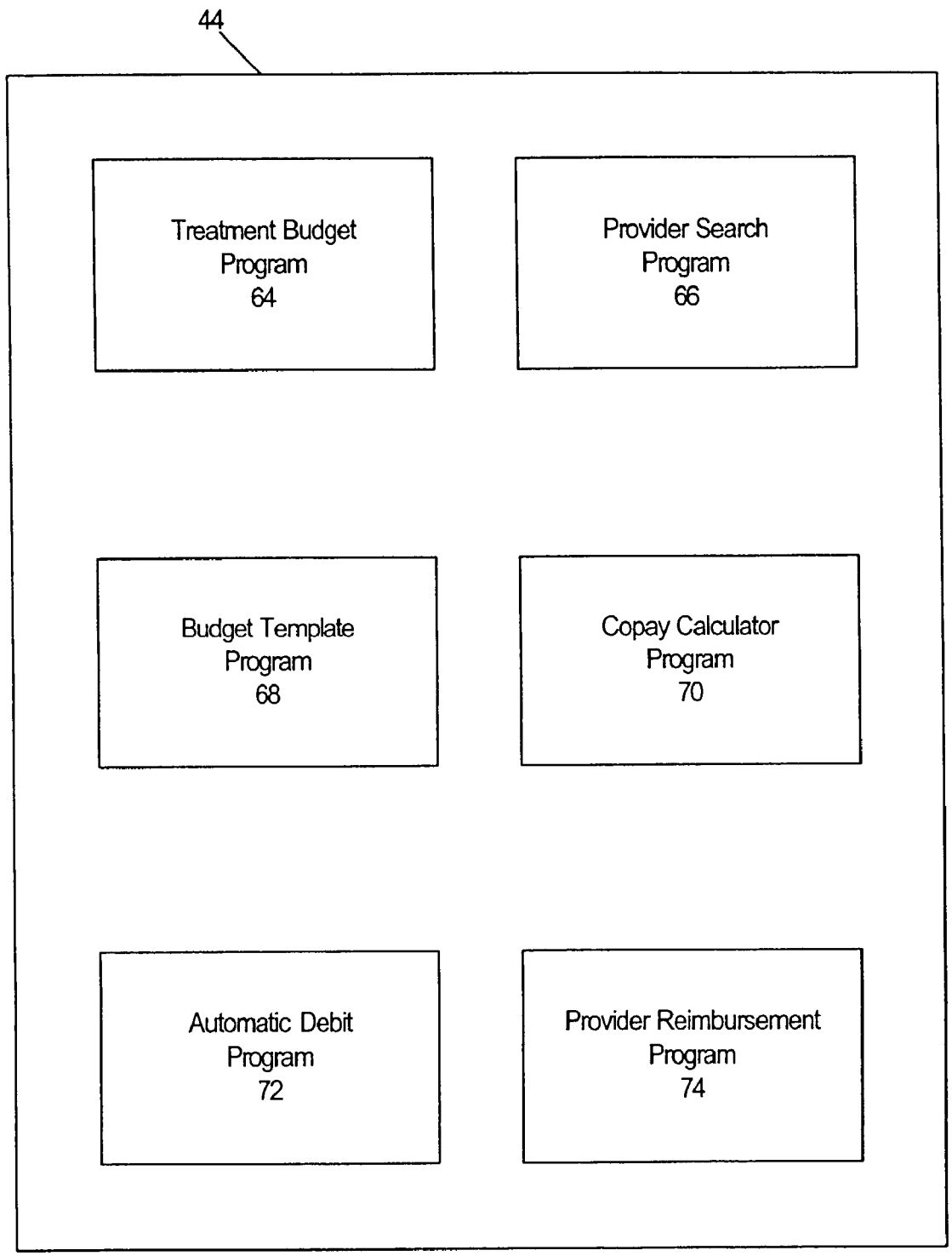
FIG. 3 is a diagrammatic view of the programs available on the Application server of the System.

FIG. 3 shows programs that are run from Application server(s) 44. System 30 may use more than one Application server 44, but here, the invention will be described using only one. Application server 44 contains Treatment Budget program 64, Provider Search program 66, Budget Template program 68, Copay Calculator program 70, Automatic Debit program 72, and Provider Reimbursement program 74. In operation, users can access and run these programs through Application server 44.

Figure 4:
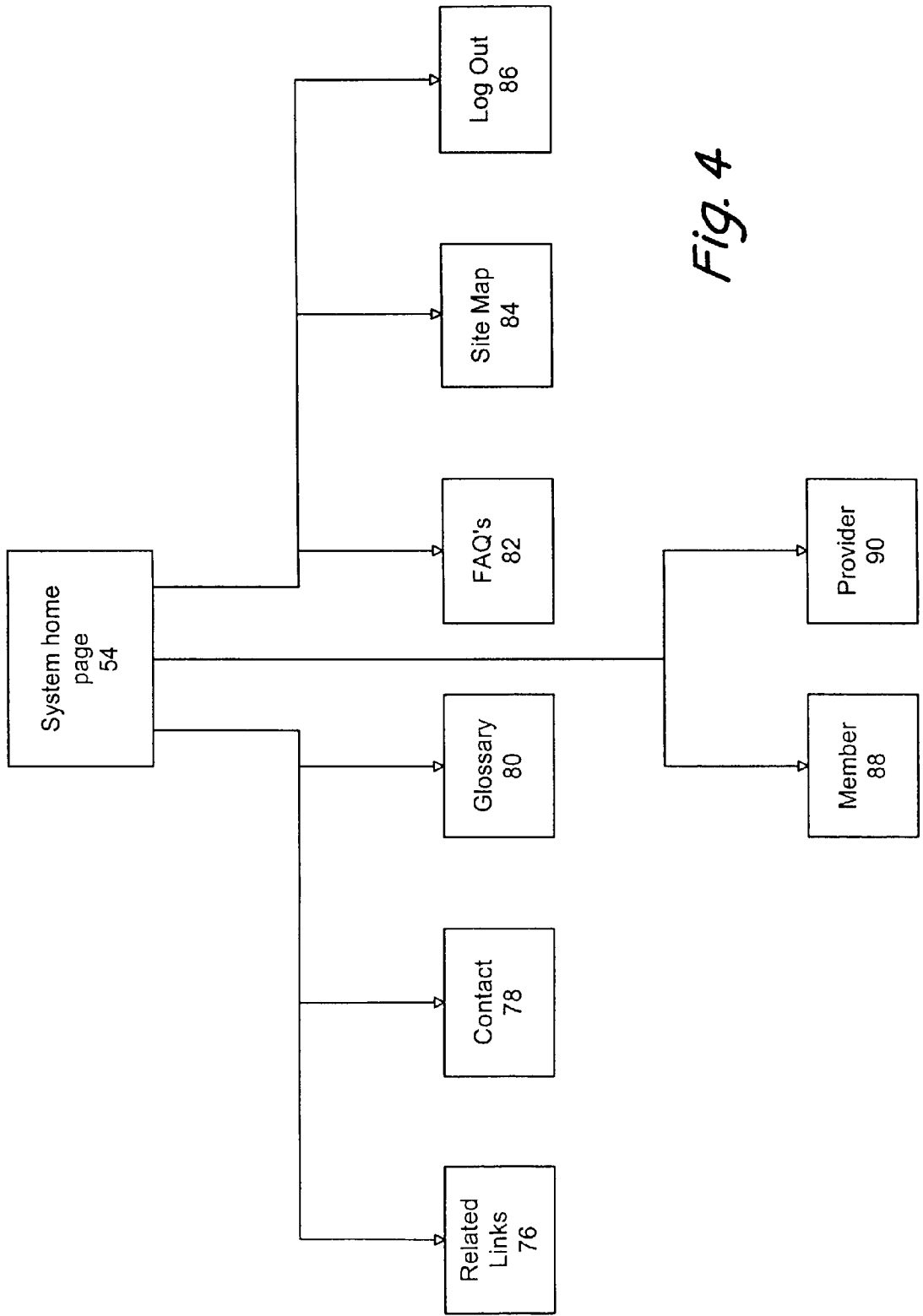
FIG. 4 is a schematic view of links associated with the System's home page.

FIG. 4 is a diagram showing how other sites from System home page 54 relate to each other after the user has logged in. These sites include Related Links link 76, Contact link 78, Glossary link 80, Frequently Asked Questions (FAQ's) link 82, Site Map link 84, Log Out button 86, Member Home Page link 88, and Provider Home Page link 90.

Figure 17:
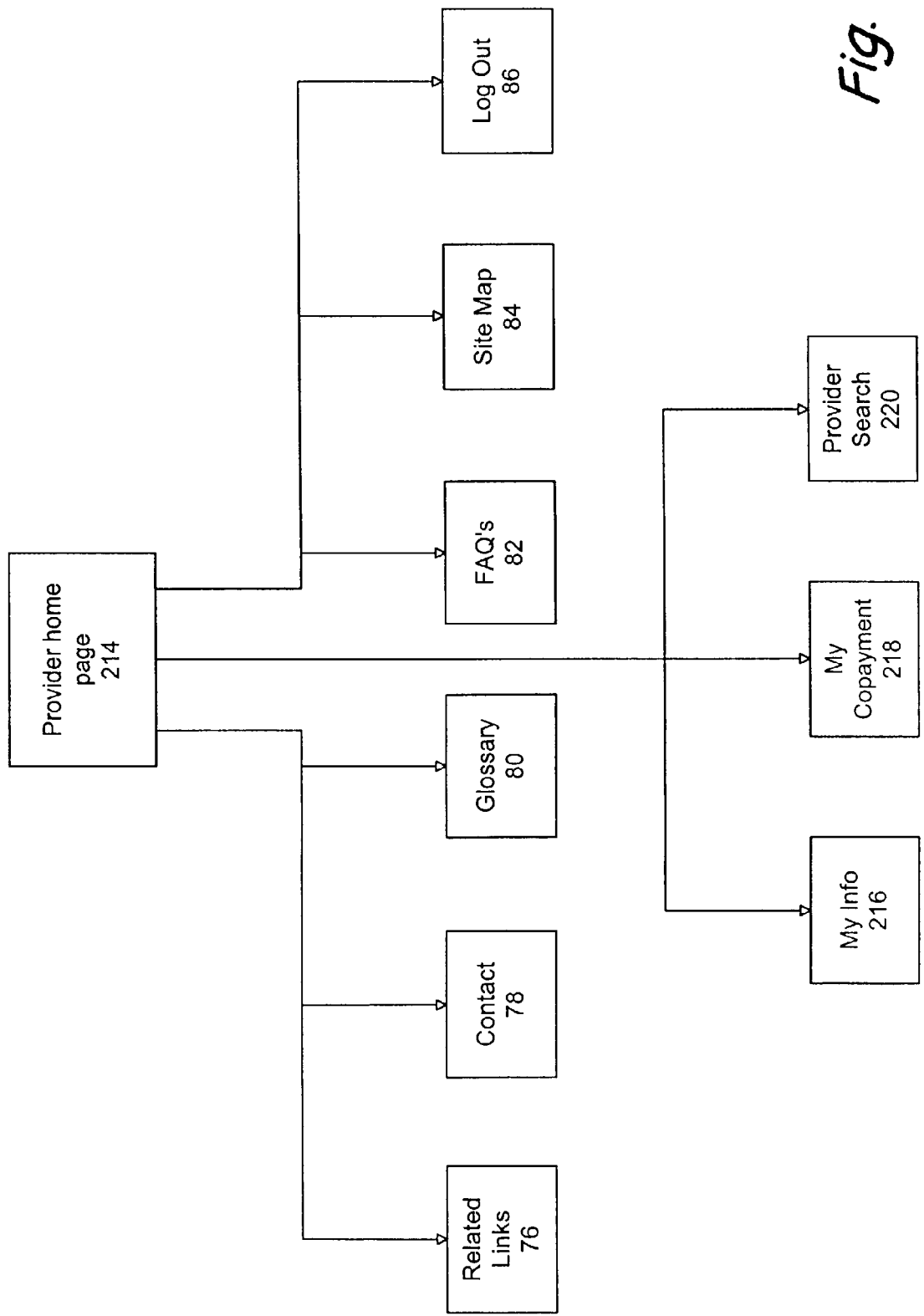
FIG. 17 is a schematic view of links associated with a Provider's home page and main topics of functions the provider can perform.

The user can click on links to access various sites. Related Links link 76 provides the user the ability to view related links at other Internet sites or other sites associated with the healthcare plan. These include links to sites that provide health information to members and library research for providers. Contact link 78 provides the ability to view information on how to contact the healthcare network for address changes, ID card requests, etc. Selecting Glossary link 80 facilitates viewing a glossary page to search for topics. FAQ's link 82 provides answers to frequently asked questions. Site Map link 84 allows the user to view a site map that provides links to all sites within System 30 that the user can access. Log Out button 86 allows the user to log off. Member Home Page link 88 provides a link to a member's Personal home page 92 (FIG. 5), and Provider Home Page link 90 provides a link to a provider's Personal home page 214 (FIG. 17). Once the user has successfully logged in, Personal home pages 92 and 214 provide the user with various links to relevant sites. The member's aspect of System 30 will be discussed first.

Figure 5:
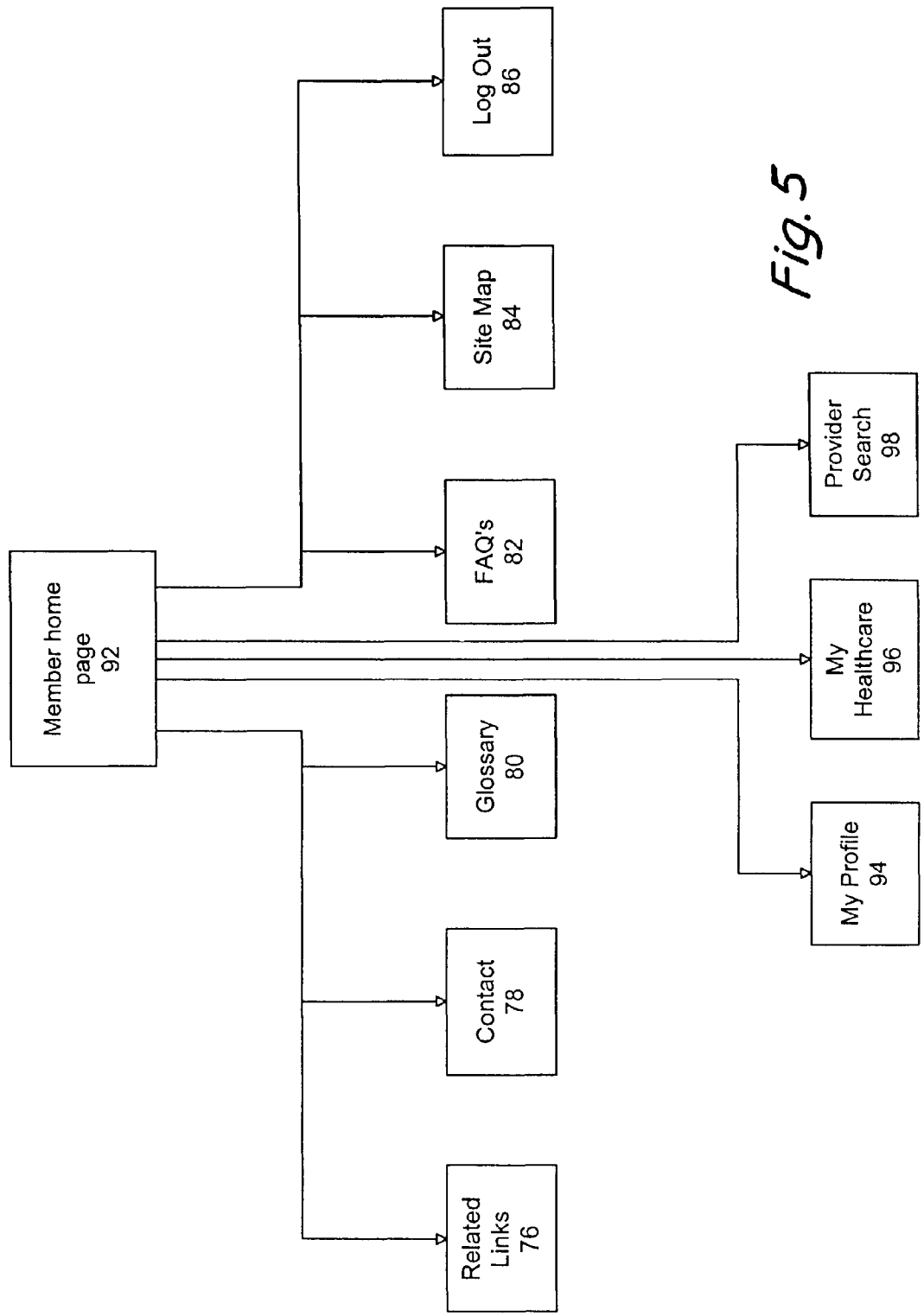
FIG. 5 is a schematic view of links associated with the member's Personal home page and main topics of functions the member can perform.

FIG. 5 shows the main topics, for which links are provided, that the member can choose from within a Navigation bar 56. These topics include My Profile 94, My Healthcare 96, and Provider Search 98.

Figure 6:
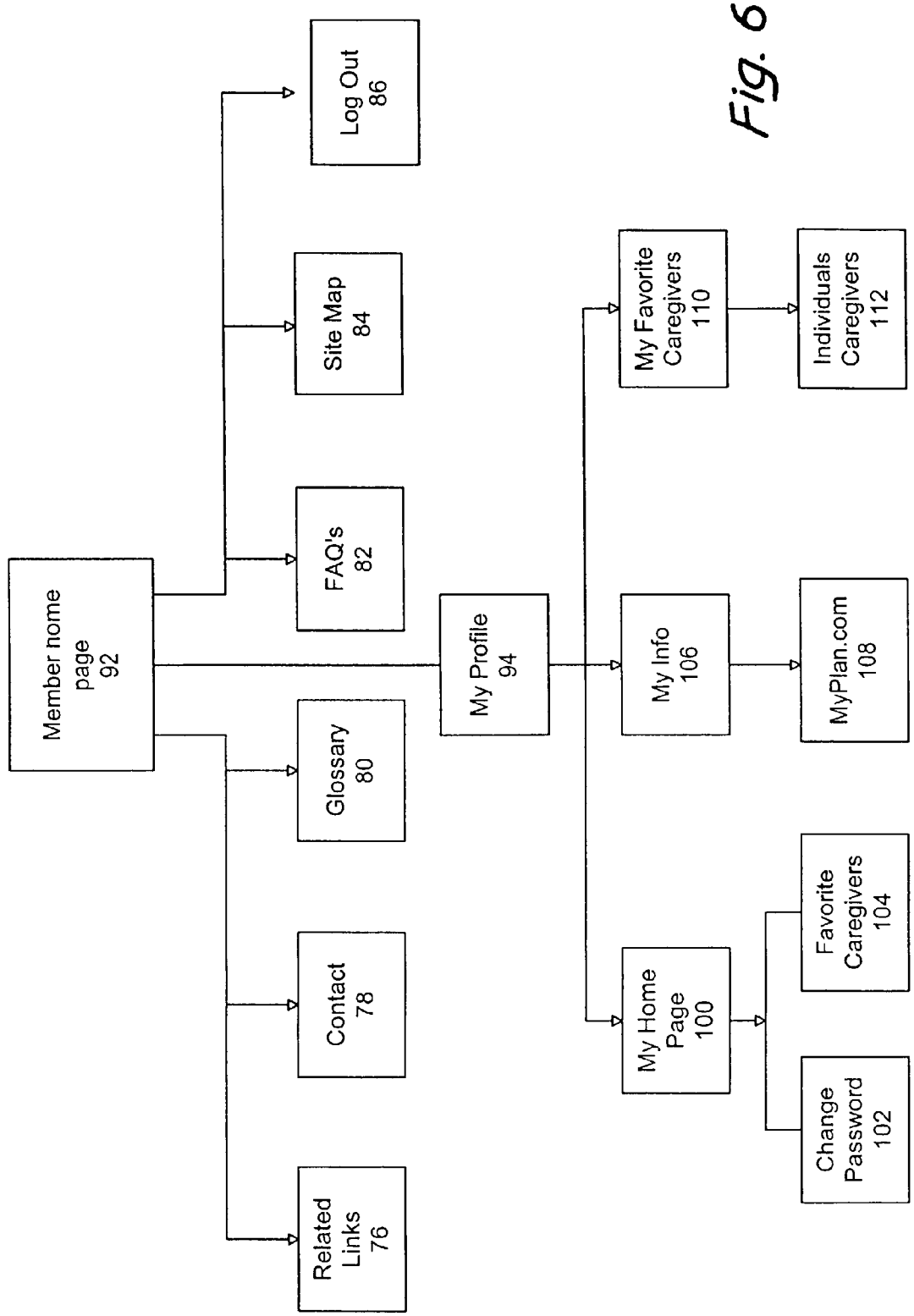
FIG. 6 is a schematic view of links and pages that can be accessed under the My Profile main topic.

Links included under My Profile 94 relate to personal information about the member. The related links are shown in FIG. 6. My Home Page link 100 provides a link that connects the member back to Personal home page 92. Clicking My Home Page link 100 allows the member to access Change Password link 102 and Favorite Care Givers link 104. Change Password link 102 accesses the appropriate site for the member to change his/her password. Favorite Care Givers link 104 provides the member with a link to a listing of the member's and member's family's favorite care givers.

My Information link 106 with MyPlan.com link 108 provide a link to the member's information pages. The information includes personal information about the member such as home and work addresses, telephone numbers, etc. and information about the member's health plan.

My Favorite Caregivers link 110 launches Individuals and Respective Caregivers page 112. Page 112 provides access to a list of System 30 user's favorite caregivers and to a list of favorite caregivers for individuals within a member's plan. This list may be edited from page 112.

Figure 7:
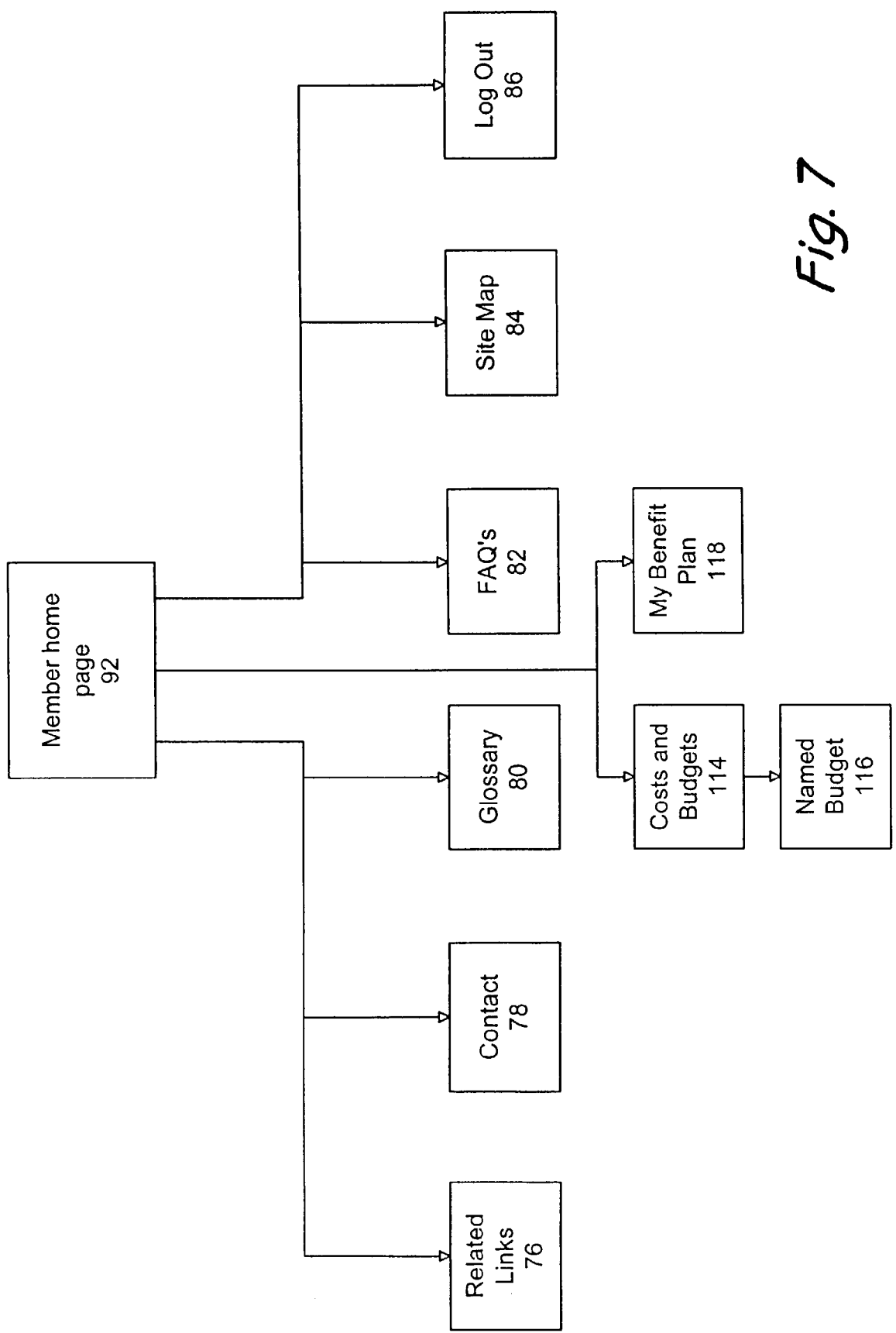
FIG. 7 is a schematic view of links and pages that can be accessed under the My Healthcare main topic.

My Healthcare 96, shown in FIG. 5, has a link to Healthcare Costs and Budgets page 114 (FIG. 7) to calculate the cost of a treatment plan. Alternatively, if the member has already calculated and saved a budget for a treatment plan, Named Budget link 116 allows the member to access this previously calculated budget plan. My Healthcare 96 also has My Benefit Plan link 118, which launches a site that describes the member's benefit plan.

Figure 8:
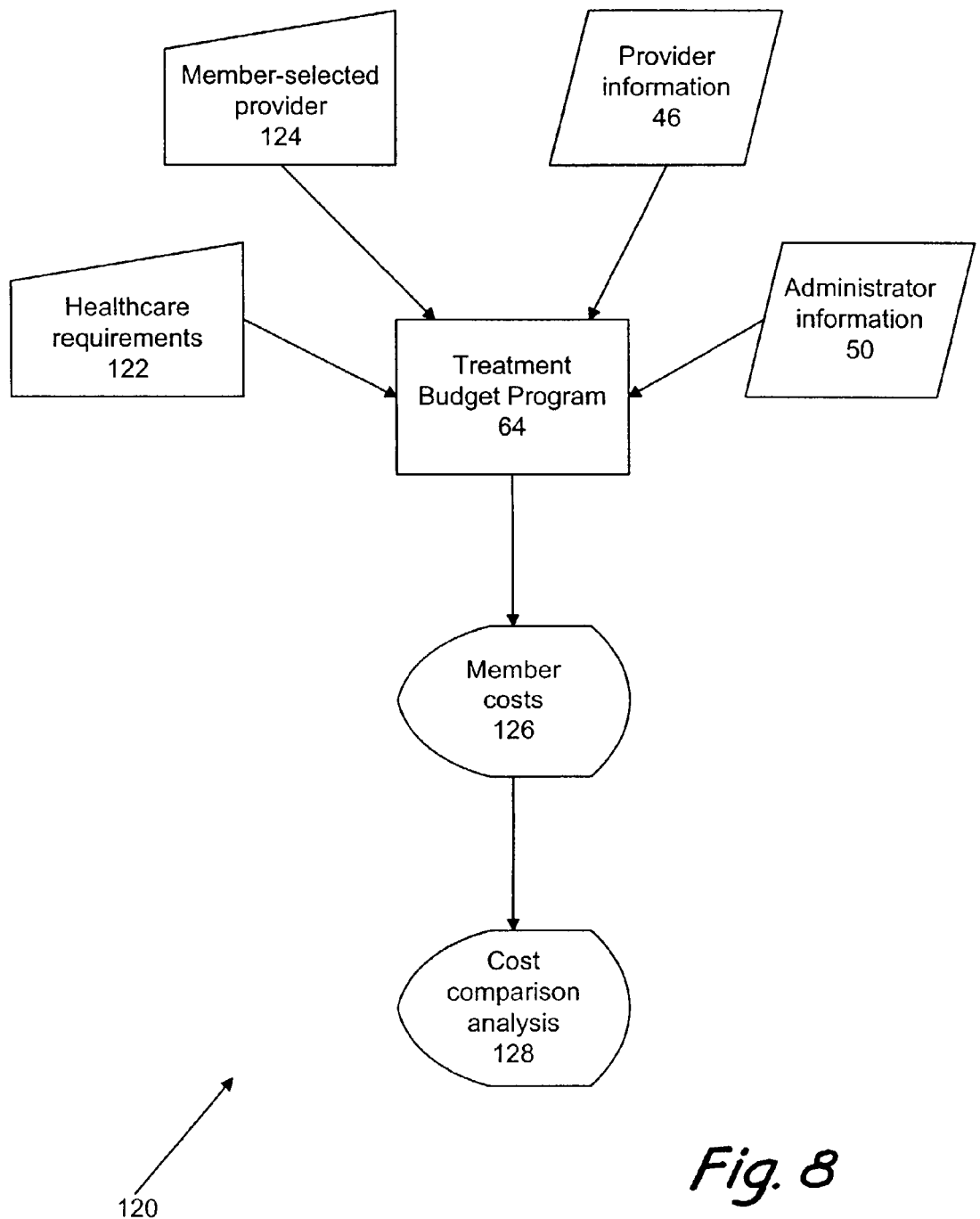
FIG. 8 is a diagrammatic view showing the function of the Treatment Budget Program.

FIG. 8 is an illustration of a process for creating a treatment budget, which calculates the cost of various treatments using selected providers and displays a cost comparison of the treatment budgets. Budget diagram 120 includes Healthcare requirements 122, Member-selected provider 124, Provider Information database 46, Administrator Information database 50, Treatment Budget program 64, Member costs 126, and Cost Comparison analysis 128.

To perform this function, members enter information relating to elements of care required for a treatment, which is represented by Healthcare requirements 122. Members must also select a provider and enter that information into program 64 as represented by Member-selected provider 124. To perform, program 64 also accesses Provider Information database 46 for copayment levels (cost-share levels or individual contribution levels) and Administrator Information database 50 for information about a treatment. Treatment Budget program 64 uses the inputs to calculate Member costs 126 for particular treatments. Program 64 will then compare that cost to the cost of doing the same treatment with other providers, as represented by Cost Comparison analysis 128.

Figure 9:
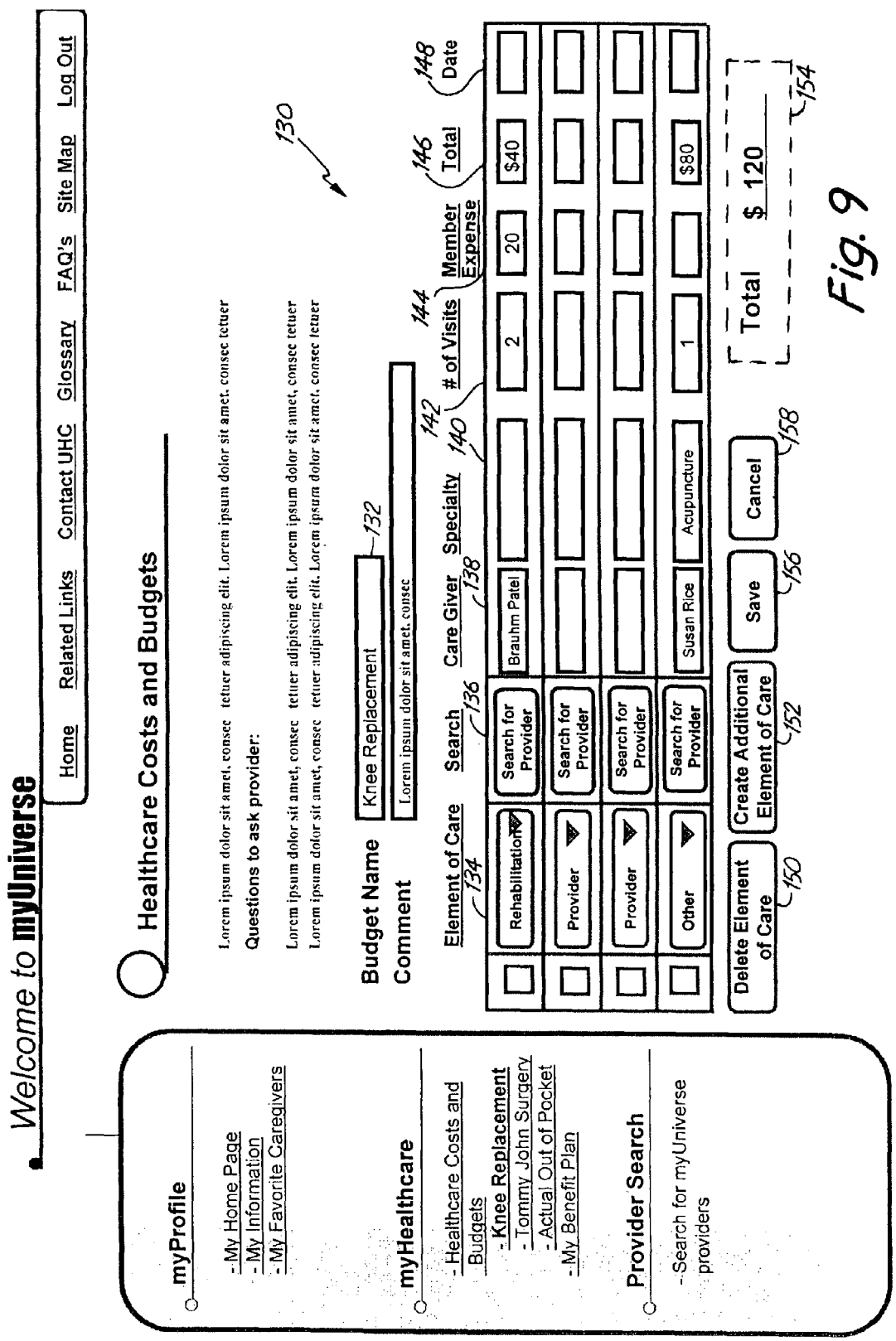
FIG. 9 is a sample screen used to calculate a treatment budget.

FIG. 9 is a sample screen that demonstrates the steps for creating treatment budgets. It contains Treatment Budget page 130 with Budget Name field 132, Element of Care drop-down menus 134, Provider Search buttons 136, Caregiver fields 138, Caregiver's Specialty fields 140, Number of Visits fields 142, Member Expense fields 144, Total Expense fields 146, Date fields 148, Delete Element button 150, Add Element button 152, Treatment Total field 154, Save button 156, and Cancel button 158.

The name of the budget is entered into Budget Name field 132, which in this example is "knee replacement". The member develops a list of each element needed for the treatment through selection from Element of Care drop-down menus 134. In this example, the member has selected rehabilitation as an element needed for treatment. Guidelines are displayed that offer advice on determining elements of care for particular treatments and what each element requires.

Provider Search buttons 136 link to a provider search site from which the member can select a care giver for a particular element. Once a care giver is selected, as will be discussed below, the member can add that information to the treatment budget.

Caregiver fields 138 list the names of the caregivers that have been chosen by the member. A favorite care giver for a particular element of treatment may automatically appear if the member has a preference, or a care giver will be added once the member has selected a care giver from a provider search. The specialty of the selected care giver is listed in Specialty field 140 next to the caregiver's name.

Number of Visits fields 142 shows how many times the member will be required to see the caregiver for a particular element of treatment. Next, the member's cost per visit is listed in Member Expense fields 144. The total expense for a particular treatment element is calculated and listed in Total Expense fields 146 as of a particular date, which is given in Date fields 148. The date may be important, because the copayment a member must pay the provider may change before the relevant time period during which the treatment will take place. It may also be important if the status of a provider either belonging to the health plan or not may change before the relevant time period. Once all the elements and caregivers have been entered, the total cost for the treatment is calculated and shown in Treatment Total field 154.

The member may customize and change the treatment budget by deleting or adding elements to the treatment budget. To delete an element of care, the member selects or highlights the element of care to be removed and clicks Delete Element button 150. The element is removed from the treatment budget and a new treatment total is calculated and shown in Treatment Total field 154.

The member may also add elements of care to the treatment budget. The member clicks on Add Element button 152. An additional row of fields and buttons will appear as described above that allows the member to select a caregiver. A new treatment total is calculated and shown in Treatment Total field 154.

Additionally, each field is editable in order to customize the treatment budget, except information entered automatically via a provider search. Save button 156 allows the member to save the treatment budget. The member can also save a work-in-progress and return later to resume work. Cancel button 158 allows the member to quit the treatment budget.

Figure 10:
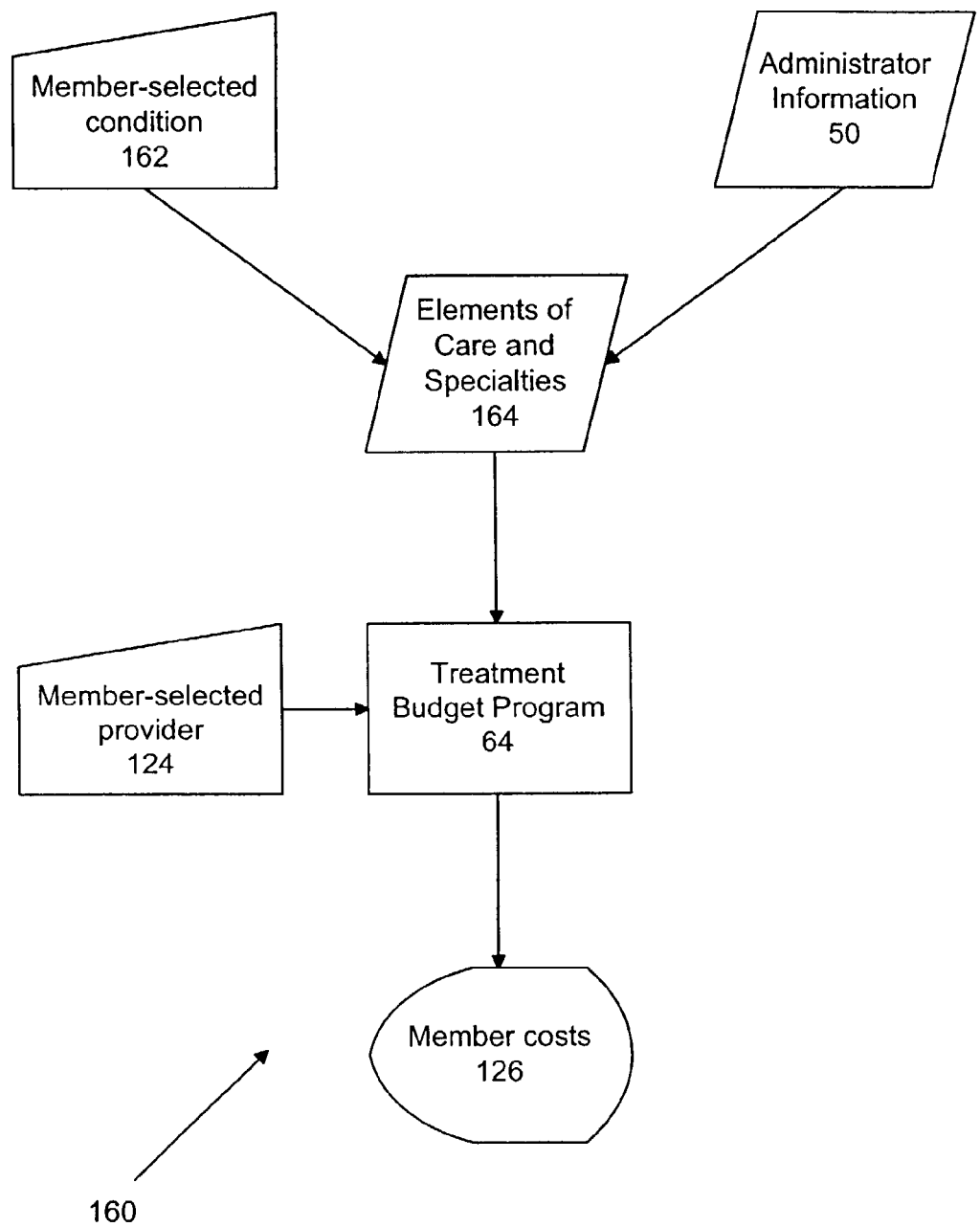
FIG. 10 is a diagrammatic view of an alternate embodiment of the Treatment Budget Program.

FIG. 10 shows an alternate embodiment of Treatment Budget program 64 wherein required elements of care for popular treatments are automatically provided to the member. Diagram 160 includes Member-selected condition 162, Elements of care and specialties 164, Administrator Information database 50, Treatment Budget program 64, Member-selected provider 124, and Member costs 126.

Here, the member selects a condition to create a treatment budget for, as represented by Member-selected condition 162. Required Elements of care and specialties 164 for the particular Member-selected condition 162 are derived from Administrator Information database 50 and entered into Treatment Budget program 64. The member next enters Member-selected provider 124 to program 64, which calculates and displays Member costs 126 for the particular treatment. The member may also search for providers for each element of care as will be discussed below.

FIG. 11 further illustrates this embodiment of System 30. FIG. 11 includes Elements of Care field 166, Provider field 168, and Select buttons 170. In the example shown in FIG. 11, the member has chosen to create a treatment budget for a knee replacement. Each required element of care is listed in Elements of Care field 166. If the member has previously chosen a favorite provider for any of the elements of care, those will be listed in Provider field 168. The member will, however, be given the choice of changing providers if desired. Provider field 168 will indicate if no favorite provider has been selected and the member will click the appropriate Select button 170 to begin a search for a provider. The listed elements would be what is typically required, and the member could change any aspect of that treatment as necessary to customize.

Preferably, the treatment budget will calculate a maximum and minimum cost to the member. Depending on factors such as the severity of a condition, the cost for certain elements of a treatment may vary. The treatment budget will calculate a range for which the treatment may cost. The cost range can also be compared to the cost of using other providers. In addition, a "health diary" to record information about the member's health and treatments can be maintained on databases 48 and 50.

Figure 12:
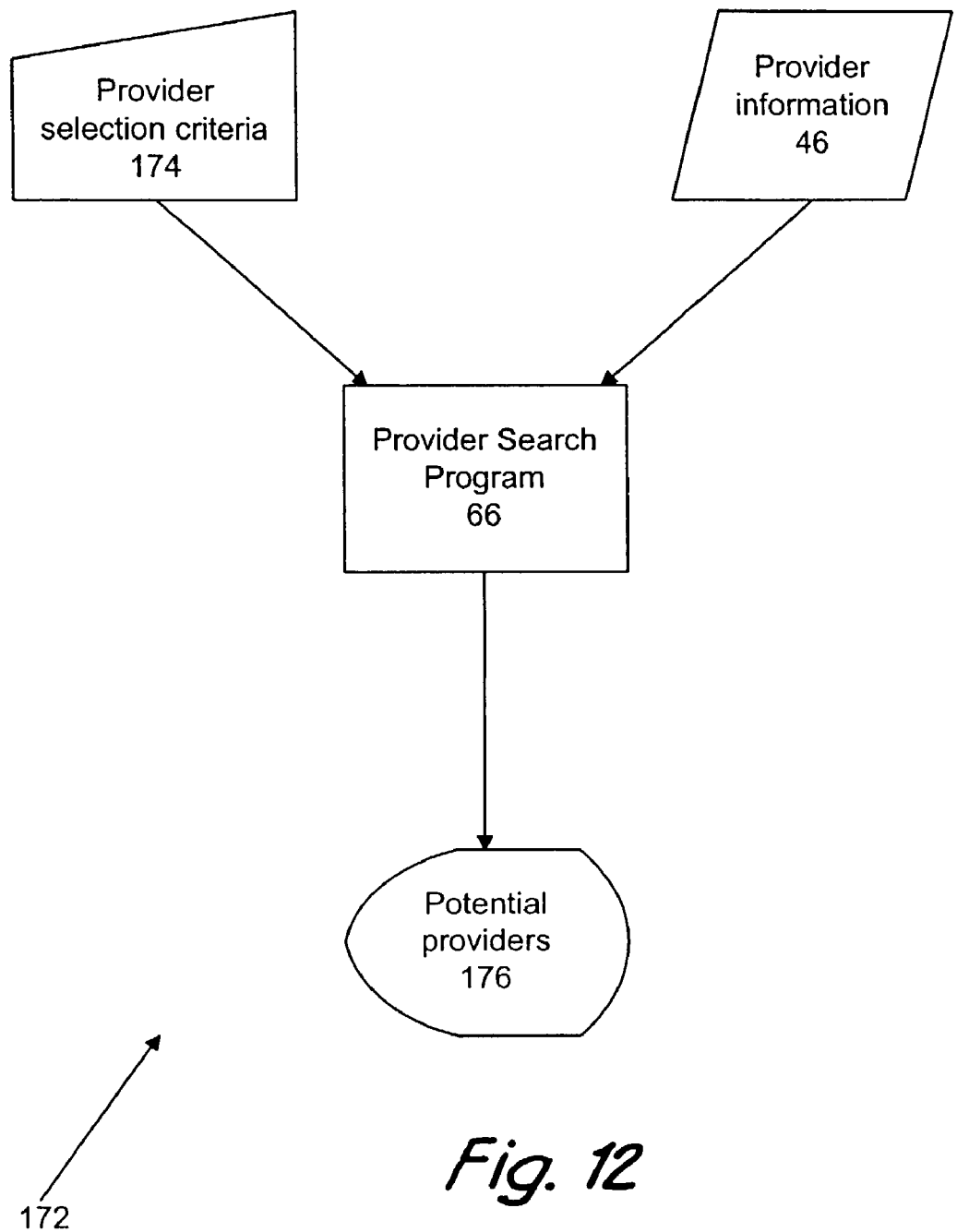
FIG. 12 is a diagrammatic view showing the function of the Provider Search Program.

The third main topic, listed in FIG. 5, of Personal home page 92 is Provider Search 98. FIG. 12 illustrates the process of performing a provider search. Provider Search diagram 172 includes Provider Selection criteria 174, Provider Information database 46, Provider Search program 66, and Potential providers 176.

In operation, a member enters requirements (inputs), represented by Provider Selection criteria 174, that the member wants Provider Search program 66 to use to find appropriate providers. Provider Search program 66 searches Provider Information database 46 and transmits Potential providers 176 that meet the selected criteria back to the member.

Provider Search 98 includes a link to access Provider Search page 178, as shown in FIG. 13, which demonstrates a search. Provider Search page 178 contains Provider Search form 180 with Location Criteria field 182, which includes Radio buttons 184A and 184B. Provider Search form 180 also includes Provider Criteria field 186, Search button 188, Clear button 190, and Results form 192 with Name links 194.

In operation, the member may choose to select a provider based on location via Location Criteria field 182. In this example, the member clicks on Radio buttons 184A or 184B to indicate whether the search should be defined by providers' locations in specific cities and states or rather in specific zip codes, respectively.

Alternatively, or additionally, the member can search by selecting criteria in Provider Criteria field 186. In this example, members can select by entering a provider's last name and/or indicating a specialty, language spoken, and/or gender. In a preferred embodiment, members can also select a provider based on practice characteristics, which were previously described. Once the criteria is selected, the member clicks on Search button 188 to enable a search. The member can also clear Criteria fields 182 and 186 by clicking Clear button 190.

The results of the search are displayed in Results form 192. In this example, a partial profile of providers that meet the criteria are listed. Name links 194 are links to Provider's Profile page 196, which displays a full profile of the provider. Comparative information about practice characteristics of potential providers may also be transmitted to the member to assist in selecting a provider.

FIG. 14 is a sample screen of Provider's Profile page 196. Provider's Profile page 196 contains Profile form 198, Treatment Budget Addition button 200, and Favorite Provider Addition button 202.

The member can decide whether or not to select the provider based on these profiles. In addition, preferred embodiments of System 30 allow members to enter and view information about the satisfaction of providers. The member may add the provider to a treatment budget if the search was done to calculate a treatment budget by clicking Treatment Budget Addition button 200. Alternatively, the member may wish to add the provider to the member's list of favorite providers by clicking on Favorite Provider Addition button 202.

Using System 30, the member can at least estimate, if not know exactly, how much a treatment will cost even before undergoing the treatment. It gives members flexibility to decide how much they want to spend and a simple means to adjust a treatment plan around that cost. Additionally, System 30 will furnish information on how to contact the healthcare plan when the member believes that the out-of-pocket maximum has been met.

Figure 15:
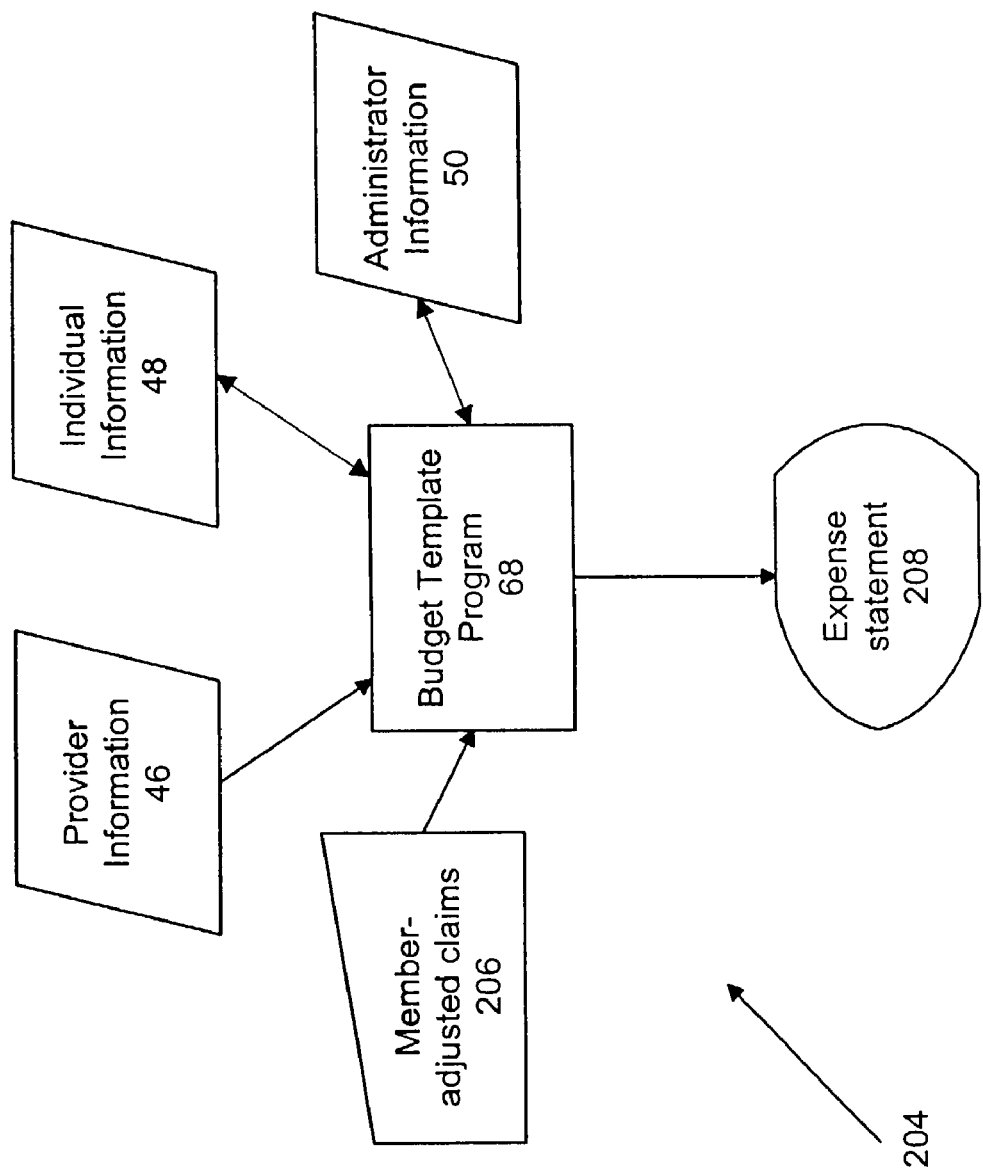
FIG. 15 is a diagrammatic view showing the function of the Budget Template Program.

FIG. 15 shows the steps involved in tracking member out-of-pocket expenses. Expense Tracking diagram 204 includes Member-adjusted claims 206, Provider Information database 46, Individual Information database 48, Administrator Information database 50, Budget Template program 68, and Expense statement 208.

To track, a member enters information regarding claims, represented by Member-adjusted claims 206, to System 30. Members can add a claim, or the member can change or delete an existing claim stored in Individual Information database 48. Previously paid copayment information is also accessed from Individual Information database 48. Budget Template program 68 uses this information, plus copayment information from Administrator Information database 50, to calculate current total out-of-pocket expenses accrued by the member. Program 68 transmits Expense statement 208, which contains the calculated total amount, back to the member. Expense statement 208 can also be transmitted to and stored in Individual Information database 48 and Administrator Information database 50.

Figure 16:
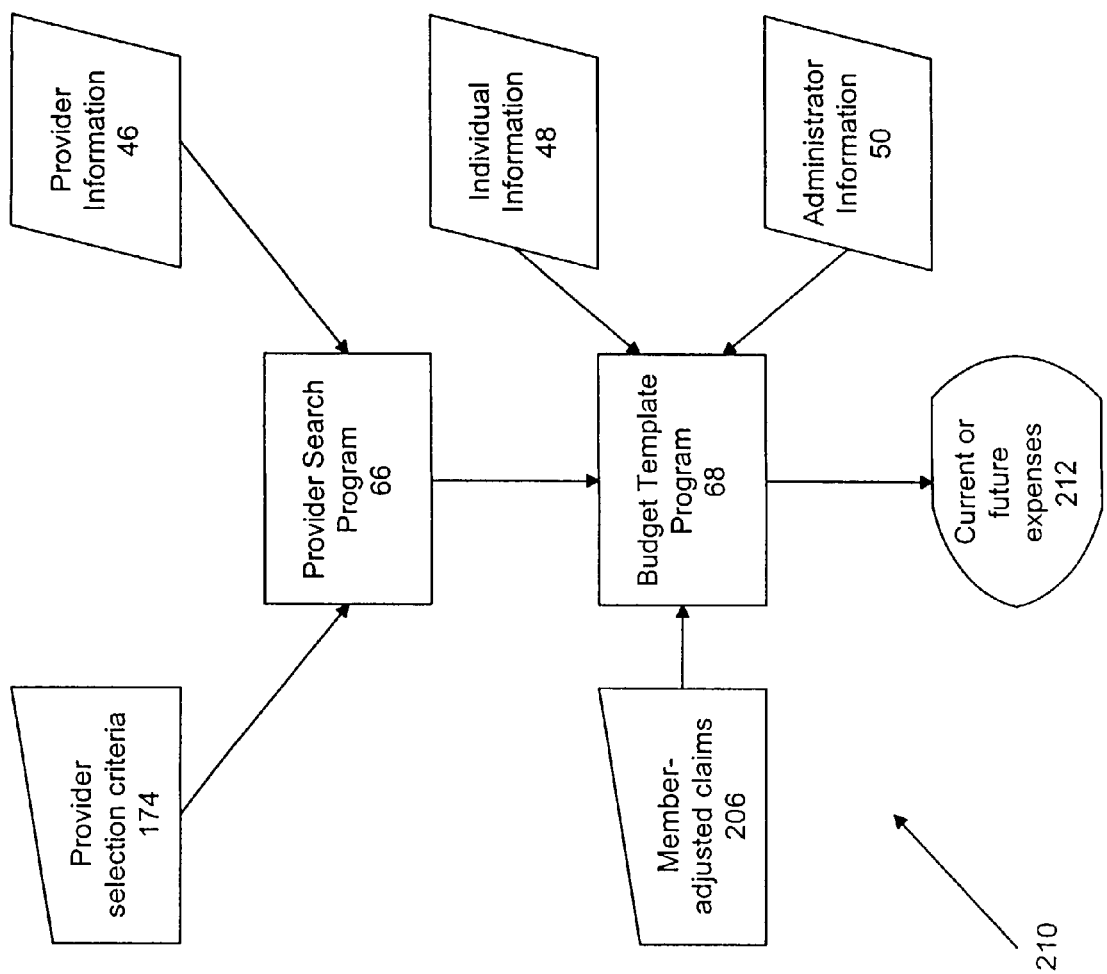
FIG. 16 is a diagrammatic view showing a preferred embodiment of the System, which combines the Provider Search Program and the Budget Template Program.

In the preferred embodiment, System 30 combines the functions of Provider Search program 66 and Budget Template program 68 to track current and future expenses. This embodiment is illustrated by Tracking diagram 210 of FIG. 16. Tracking diagram 210 includes Provider Search program 66, Provider Search criteria 174, Provider Information database 46, Budget Template program 68, Member-adjusted claims 206, Individual Information database 48, Administrator Information database 50, and Current or Future expenses 212.

Provider Search program 66 uses Provider Selection criteria 174 to select a provider from information stored in Provider Information database 46 as previously described. The results are entered into Budget Template program 68. The member enters Member-adjusted claims 206, and program 68 uses this information plus information obtained from Individual Information database 48 and Administrator Information database 50, as described above, to calculate Current or Future expenses 212. Current or Future expenses 212 is transmitted back to the member to be saved in Individual Information database 48.

In the preferred embodiment, customer service representatives of the healthcare plan will be able to access the site in the same way that a user does in order to see the site as they are trouble-shooting for a user. The representatives may also access System 30 on behalf of a user that is unable or unwilling to use System 30 him/herself. System 30 will log that a representative is taking action on behalf of the user. This service functions for both members and providers.

The provider aspect supplies another part of System 30 and will be discussed next. Provider Home Page link 90, shown in FIG. 4, links a provider to the provider's Personal home page 214. FIG. 17 shows the main topics the provider can access on a Navigation bar 56. These topics include My Information 216, My Copayment 218, and Provider Search 220.

Figure 18:
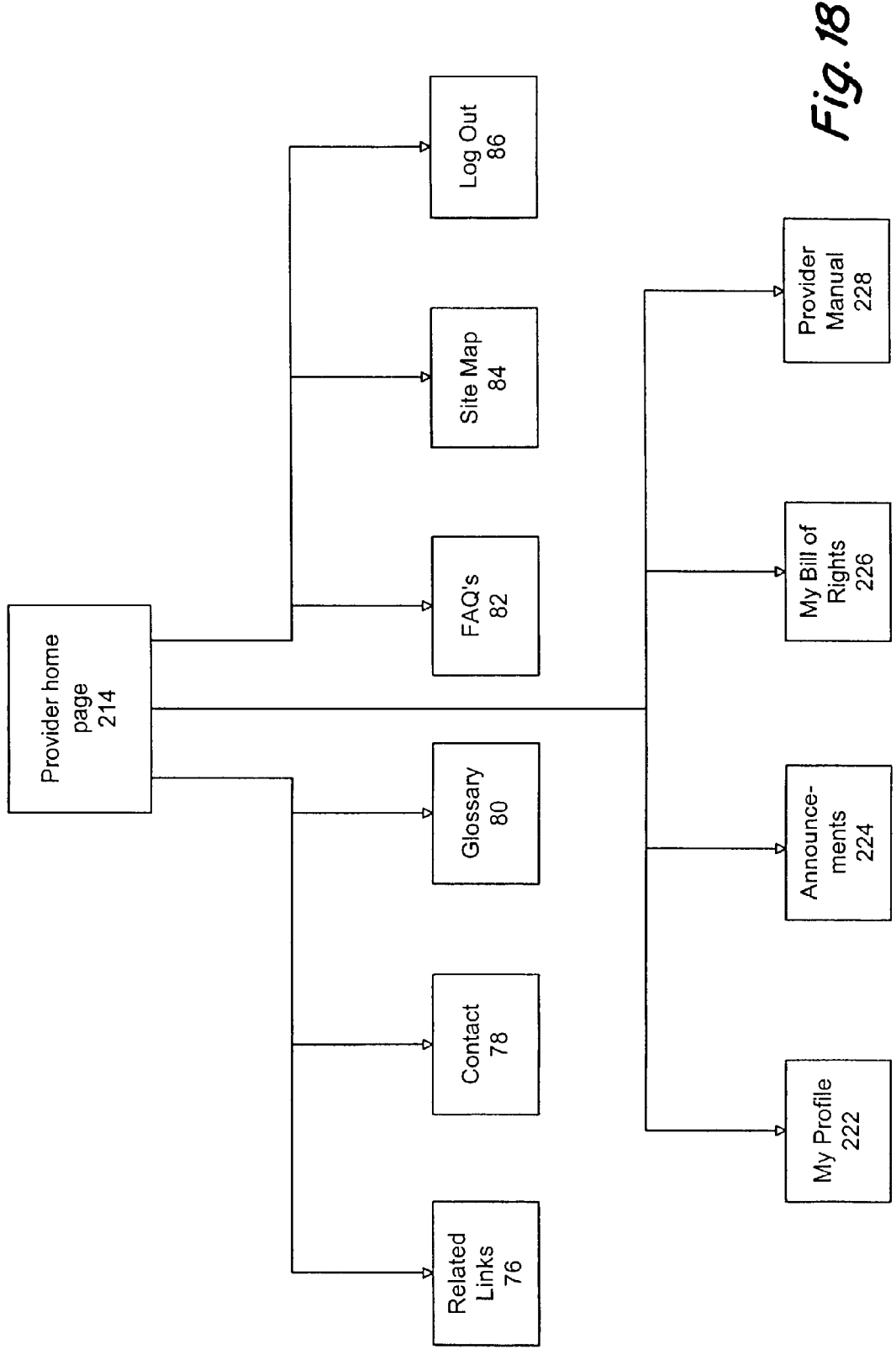
FIG. 18 is a schematic view of links that can be accessed under the My Information main topic.

My Information 216 has corresponding sub-topics as shown in FIG. 18. These sub-topic links allow the provider to gain access to relevant sites. This example includes My Profile link 222, My Announcement link 224, My Bill of Rights link 226, and My Provider Manual link 228. Other embodiments may include other main topics and sub-topics. My Bill of Rights link 226 and My Provider Manual link 228 may optionally be omitted.

My Profile link 222 furnishes a link to Provider's Profile page 196, shown in FIG. 14. However, the provider is allowed to edit and update at least some of the information contained in Profile form 198. The information entered by the provider in Profile form 198 supplies the practice characteristics for provider searches. Providers may also be given an email address through the web site where members can contact them. Preferably, providers that do not belong to the healthcare plan will also be allowed to create a profile.

In the preferred embodiment, providers can show announcements they wish users to read. My Announcements link 224 links to a page where the provider can create an announcement, view an existing announcement, or edit or cancel an existing announcement. Announcements are subsequently posted for users to read.

Optionally, providers will also have access to a provider's bill of rights through System 30. My Bill of Rights link 226 furnishes the link to a copy of the bill of rights.

Another option is to provide an electronic copy of a provider manual through My Provider Manual link 228. The preferred embodiment of the manual will include details on care coordination, provider relations, reimbursement guidelines, preventive care guidelines, claim adjudication guidelines, how to find a provider using System 30, and how to join the provider network.

Figure 19:
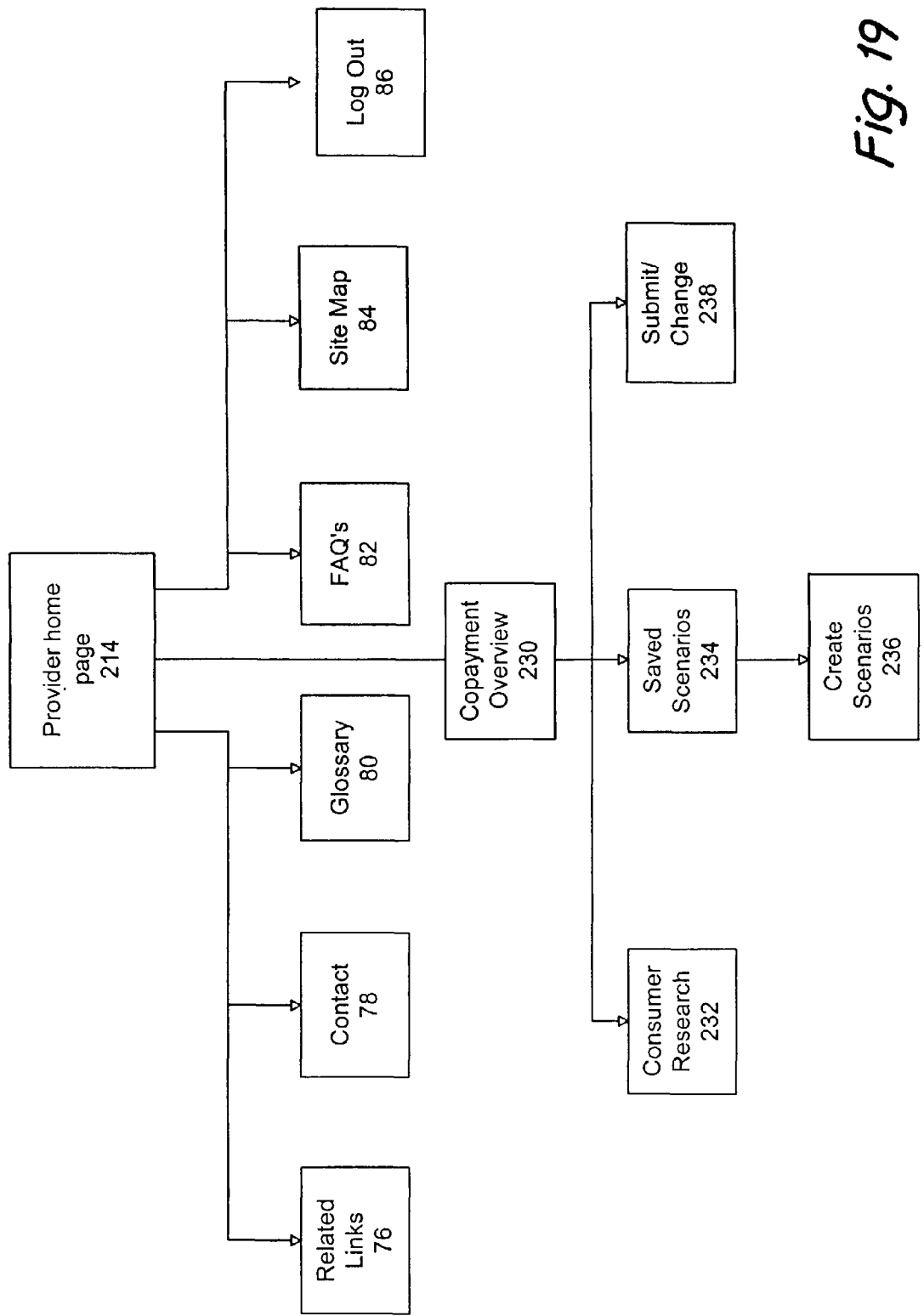
FIG. 19 is a schematic view of links that can be accessed under the My Copayment main topic.

The next main topic shown in FIG. 17 is My Copayment 218. System 30 allows providers to determine the level of copayment they wish to be reimbursed by members. In order to help providers determine what copayment level will work best, System 30 provides a method of calculating various reimbursement scenarios, which are economic analyses, that project the financial impact on the provider's practice. The corresponding sub-topic links to My Copayment 218 are shown in FIG. 19 and include My Copayment Overview Page link 230, Consumer Research link 232, Saved Reimbursement Scenarios link 234 with Create Scenario form 236, and Submit/Change Copay link 238.

Figure 20:
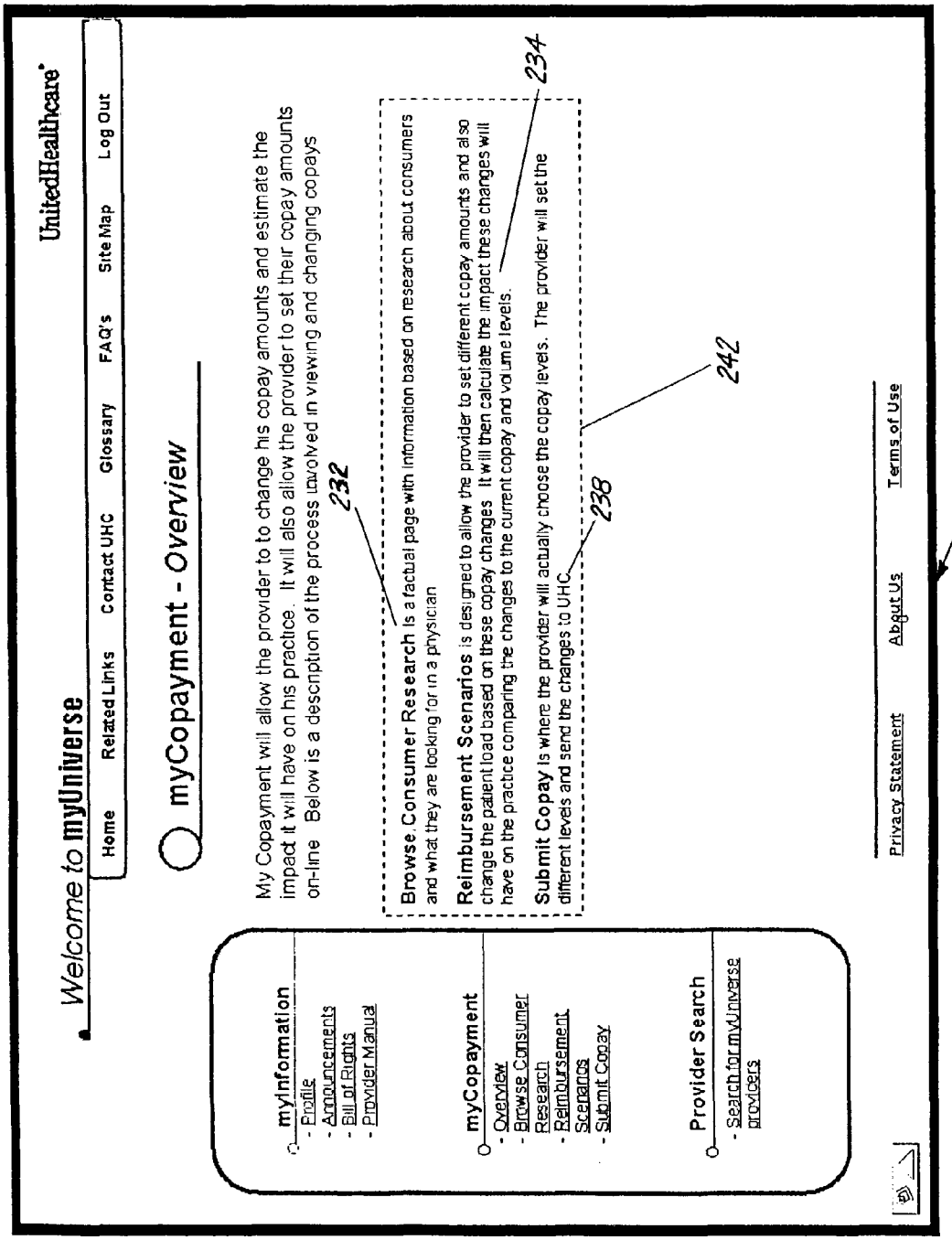
FIG. 20 is a sample screen providing an overview of choosing a copayment level.

In operation, the provider clicks on Overview Page link 230 and accesses Overview page 240. FIG. 20 is a sample screen showing an example of Overview page 240. Overview page 240 includes Instructions 242, which also furnishes links 232, 234, and 238. Static instructions are given on how to calculate reimbursement scenarios and change copayment levels. The provider can click on Consumer Research link 232, Saved Scenarios link 234, and Submit/Change Copay link 238 from within Instructions 242.

The following links relating to the provider's copayment level are accessed either through Instructions 242 or via the sub-topic links under Overview Page link 230 (FIG. 19) in a Navigation bar 56. Consumer Research link 232 accesses a site where information gathered from consumer research on provider reimbursement through copayments is shown. This information gives providers an idea of what consumers are willing to pay in order to obtain the care they want, so that an appropriate balance of desired care and copayment costs can be struck.

Figure 21:
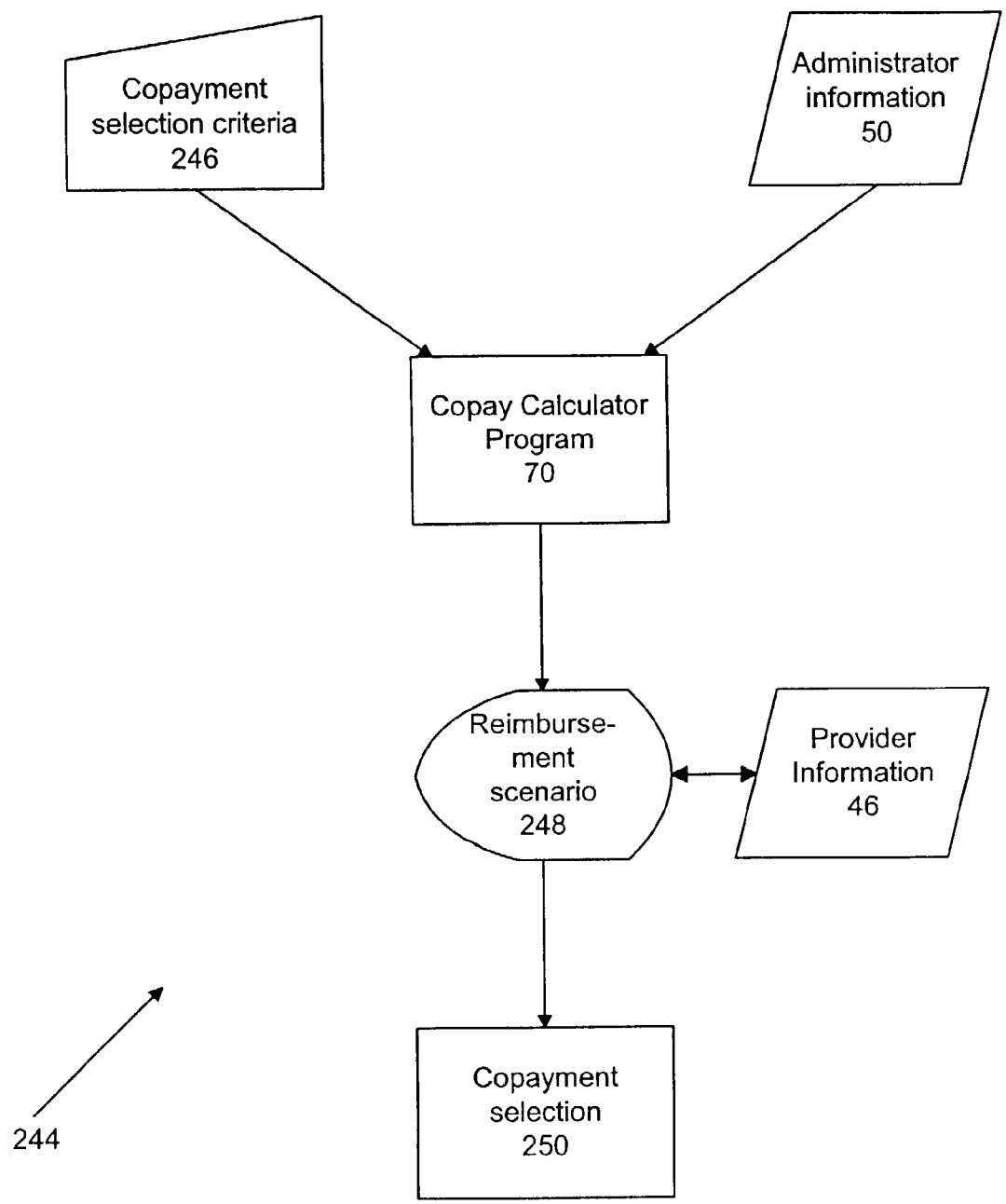
FIG. 21 is a diagrammatic view showing the function of the Copay Calculator Program.

Providers can also create reimbursement scenarios which estimate the financial impact of choosing a specific copayment level on a provider's practice and assist choosing a copayment level. FIG. 21 illustrates the process. Copayment Scenario diagram 244 includes Copayment Selection criteria 246, Administrator Information database 50, Copay Calculator program 70, Reimbursement scenario 248, Copayment selection 250, and Provider Information database 46.

To create a reimbursement scenario, a provider enters Copayment Selection criteria 246, which includes a copayment level and patient volume. Information relating to patient volumes may also be retrieved from Administrator Information database 50. Copay Calculator program 70 uses the information to calculate the financial impact on the provider's practice and transmits that information to the provider as represented by Reimbursement scenario 248. From this information, the provider chooses a copayment level as shown by Copayment selection 250, which is stored in Provider Information database 46 as a practice characteristic. Previously saved scenarios can be retrieved from Provider Information database 46 so that a provider may recalculate a new scenario from the old one.

Figure 22:
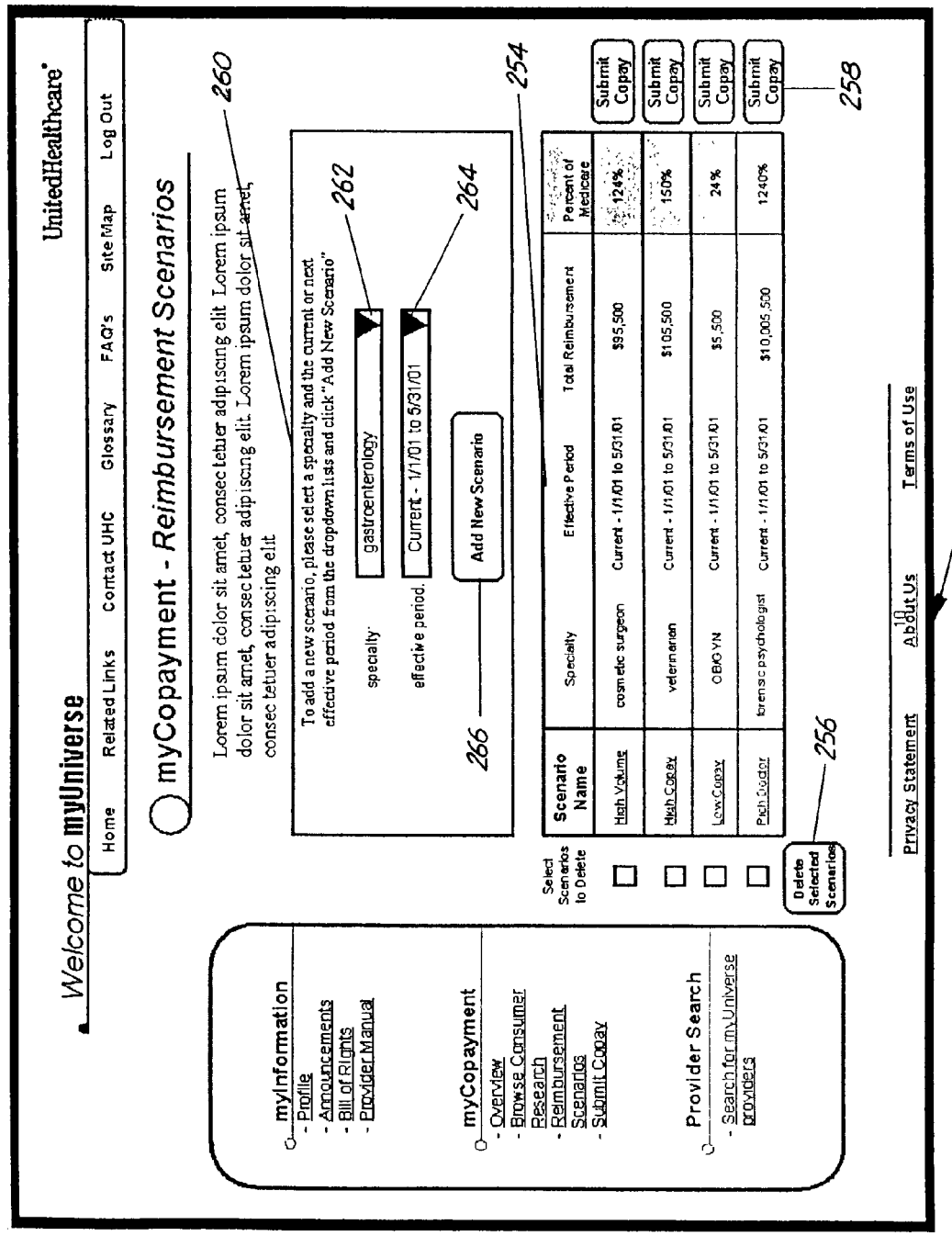
FIG. 22 is a sample screen illustrating reimbursement scenarios.

Reimbursement Scenarios link 234 (FIGS. 19 and 20) links to Reimbursement Scenario page 252, shown in FIG. 22, and further demonstrates the function of Copay Calculator program 66. Page 252 includes Saved Scenario form 254, Delete Scenario button 256, Submit Copay buttons 258, Create Scenario form 260 with Specialty and Effective Period drop-down menus 262 and 264, and Add Scenario button 266.

Any previously calculated scenarios that were saved are shown in Saved Scenario form 254. Saved Scenario form 254 displays the scenario name, specialty, effective period, total reimbursement during the effective period, and percent of Medicare. The provider can edit a saved scenario by clicking on it to launch the page where the calculations were performed, which is further described below. Saved scenarios may be deleted by highlighting or selecting a scenerio and then clicking on Delete Scenario button 256. By clicking on a corresponding Submit Copay button 258, that copayment level will be entered into Profile form 198 and used for member selection criteria where the member is searching for a provider based on cost. Additionally, the copayment level will be used to calculate treatment budgets for the member.

To create a reimbursement scenario, the provider must enter a specialty from Specialty drop-down menu 262 and effective dates from Effective Period drop-down menu 264 and click Add Scenario button 266. This launches Add Scenario page 268, which calculates the impact on the provider's practice.

Figure 23:
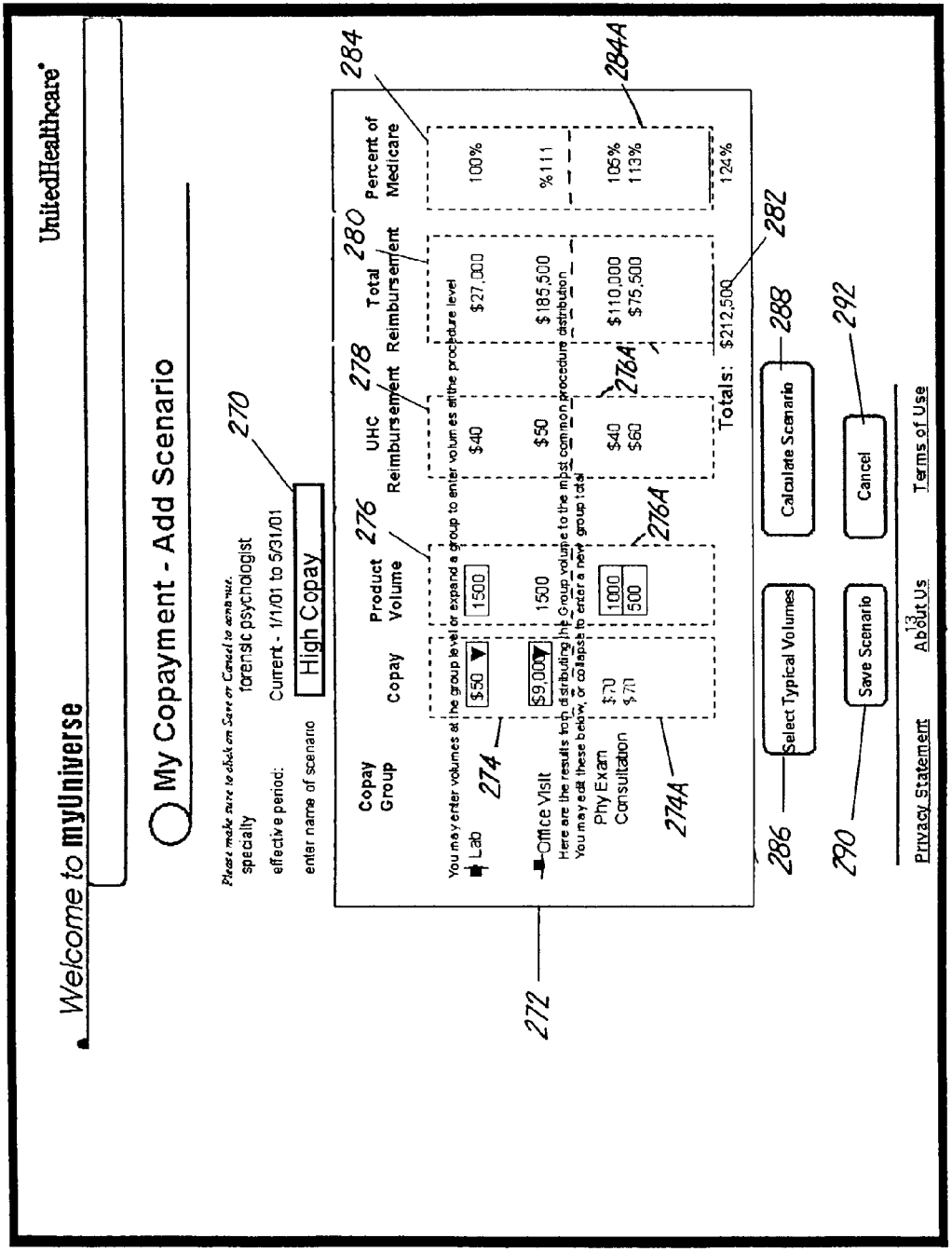
FIG. 23 is a sample screen illustrating steps in creating reimbursement scenarios.

FIG. 23 is a sample screen of Add Scenario page 268. Add Scenario page 268 includes Name field 270, Calculator form 272 with Copay fields 274 and 274A, Volume fields 276 and 276A, Plan Reimbursements fields 278 and 278A, Total Reimbursements fields 280 and 280A, Practice total 282, and Medicare Percentages fields 284 and 284A, Typical Volume button 286, Calculate button 288, Save button 290, and Cancel button 292. In the example illustrated in FIG. 23, the fields with no letter designation relate to Lab procedures, while the fields designated "A" represent Office Visit procedures.

In operation, the provider enters a name for the scenario into Name field 270. Copayment levels are entered into Copay fields 274 and 274A and patient volumes into Volume fields 276 and 276A (collectively referred to as cost-sharing selection data). The provider may wish to use known typical volumes for specific elements of care, which are automatically entered by clicking on Typical Volume button 286. Plan Reimbursement fields 278, 278A are preset and cannot be edited by the provider. Once the cost-sharing selection data is entered, totals for Total Reimbursements fields 280, 280A, Practice total 282, and Medicare Percentages fields 284, 284A are calculated and displayed by clicking Calculate button 288. Medicare Percentages fields 284, 284A represent how much the provider would receive using the reimbursement scenario compared to reimbursements from Medicare, in this example, or any other market-driven specific industry standard.

The novel fee schedule methodology described previously in conjunction with FIG. 1A and stored in Administrator Information database 50 provides the information to break down the volumes into the most common procedure distributions, which are shown in Volume field 276A. The distribution is carried out to Plan Reimbursement field 278A, Total Reimbursements field 280A, and Medicare Percentages field 284A. The provider may edit Volume field 276A to customize the scenario to fit the provider's practice.

Scenarios, either saved or just performed, can be edited by entering new values into Copay fields 274, 274A, and/or Volume fields 276, and 276A and then clicking Calculate button 288. The scenario is saved by clicking Save button 290 or canceled by clicking Cancel button 292.

When a scenario is submitted, it is listed in Saved Scenario form 254 (FIG. 22). In the preferred embodiment, the provider can also save works-in-progress and return later to resume work. As previously described, the provider can submit the copayment level by clicking corresponding Submit Copay button 258. This launches Submit Copay page 294.

FIG. 24 is a sample screen of Submit Copay page 294. It includes Specialty drop-down menu 296, Effective Date drop-down menu 298, Copay form 300 with Procedures 302, Current copays 304, and Select Copay drop-down menus 306, Submit button 308, and Cancel button 310.

If Submit Copay page 294 is launched directly by clicking Submit Copay button 258 of Reimbursement Scenario page 252 (FIG. 22), new copay levels automatically populate Select Copay drop-down menus 306. The provider can submit these levels to Profile form 198 by clicking Submit button 308 or cancel the process by clicking Cancel button 310. Alternatively, the provider may launch the page from a link in the site map or sub-topic Submit/Change Copay link 238 (FIG. 19). If the site is launched from either link, the provider must enter a specialty in Specialty drop-down menu 296 and dates in Effective Date drop-down menu 298. Preferably, Procedures 302 and Current copays 304 will automatically be listed in Copay form 300. Copayment levels are entered in Select Copay drop-down menus 306. Again, the provider can choose to submit or cancel by clicking the appropriate button. Providers may set copayment reimbursements for either their primary specialty or other secondary specialties, and optionally, reimbursements may vary for a single provider in a single specialty depending on location.

The final main topic found on the provider's Personal home page 214 is Provider Search 220 (FIG. 17). The provider's search method for a provider/consultant is identical to the member's provider search method. Refer to FIGS. 12-14 and the corresponding discussion above for a description of the search method. The provider may wish to use this feature to find a consultant or, since copayment levels are listed in the profiles, to determine copayment levels of peers.

Figure 25:
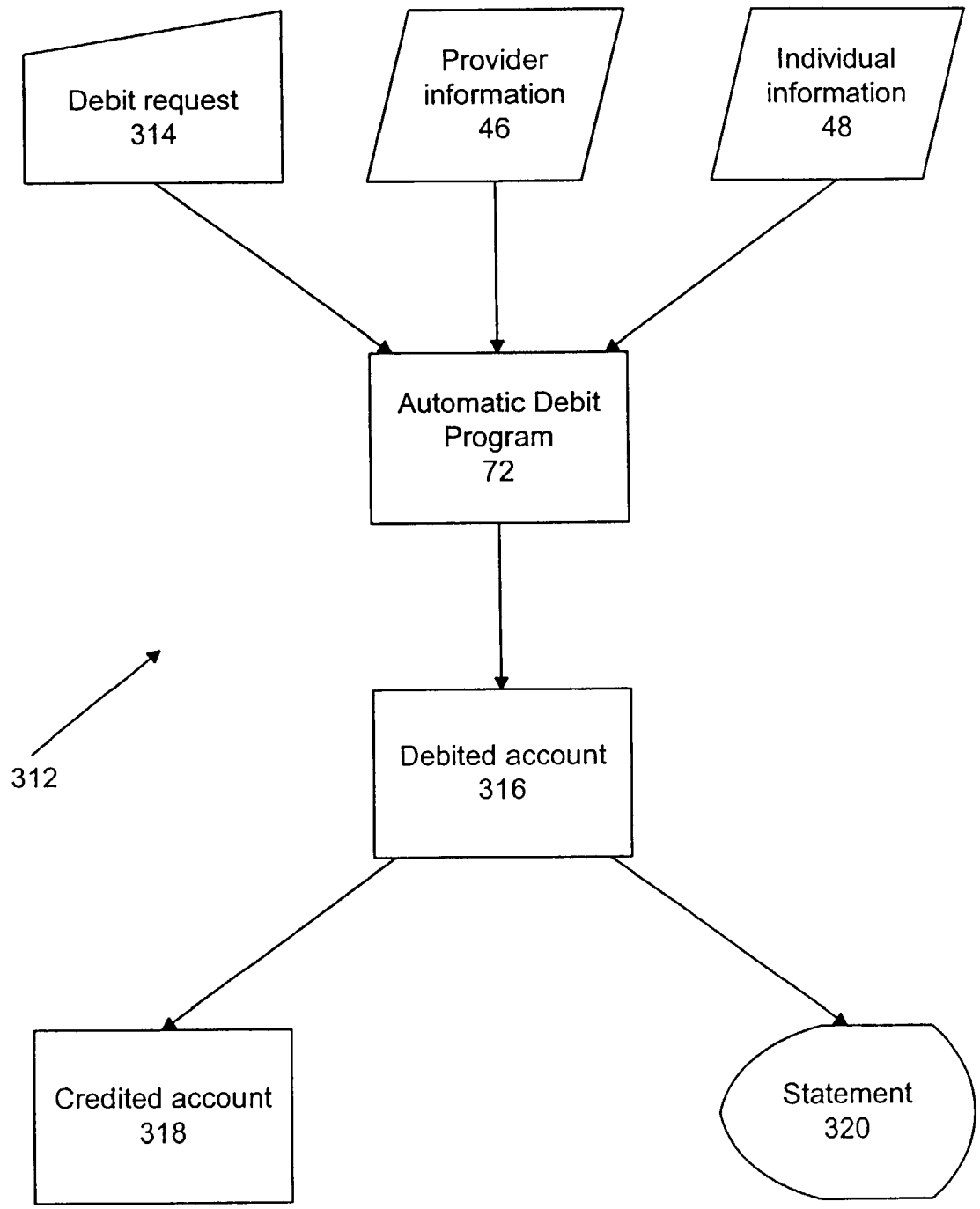
FIG. 25 is a diagrammatic view showing the function of the Automatic Debit Program.

An alternate embodiment of System 30 includes a program to automatically debit a copayment from a member's money account and transfer the copayment to the appropriate provider. FIG. 25 shows Debiting diagram 312. Debiting diagram 312 includes Debit request 314, Individual Information database 48, Provider Information database 46, Automatic Debit program 72, Debited account 316, Credited account 318, and Statement 320.

In operation, a member transmits Debit request 314 to System 30. Automatic Debit program 72 receives request 314, which are cost-share charges, and receives money account information from Individual Information database 48 and Provider Information database 46. Automatic Debit program 72 uses the information to debit the member's account as shown by Debited account 316. The copayment is transmitted to the provider's money account, which is represented by Credited account 318, and Statement 320 is transmitted to the member indicating the reduction in funds from the money account.

Figure 26:
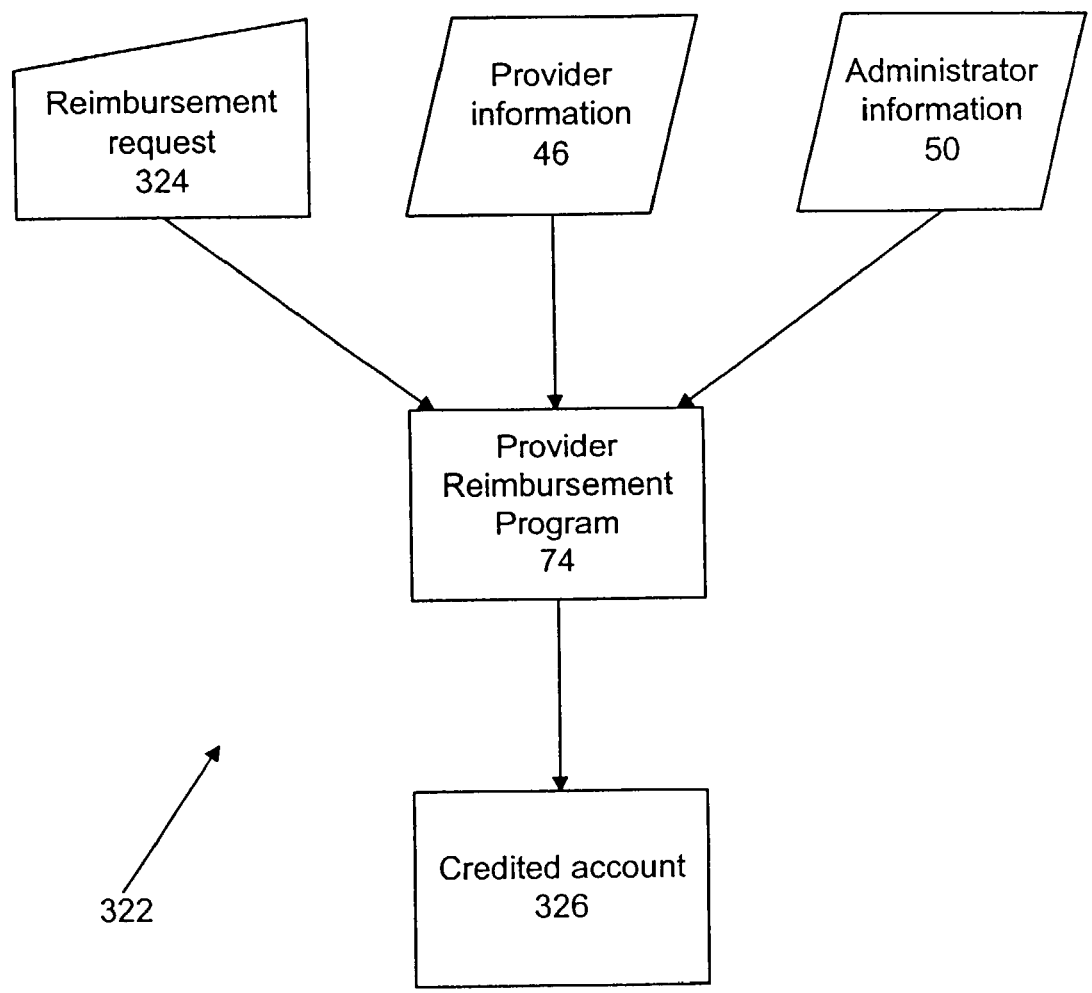
FIG. 26 is a diagrammatic view showing the function of the Provider Reimbursement Program.

In another alternative embodiment, a provider may request and receive reimbursements through System 30. FIG. 26 illustrates the process. Provider Reimbursement diagram 322 includes Reimbursement request 324, Provider Information database 46, Administrator Information database 50, Provider Reimbursement program 74, and Credited account 326.

In operation, a provider transmits Reimbursement request 324, which is either cost-share charges or fee schedule reimbursements, through System 30. Provider Reimbursement program 74 receives money account and fee schedule information from Provider Information database 46 and Administrator Information database 50. Reimbursement information is transmitted to the provider's money account as shown by Credited account 326.

In either of these alternative embodiments, System 30 may only prompt the health plan to send reimbursements, for instance, by mail. Therefore, only certain aspects of the process are performed through Network 36, and others are performed through other means.

Those skilled in the art will recognize that the sample screens provide only one example of System 30. Alternative embodiments may also be utilized and still fall within the scope of the invention.

Although the present invention has been described with reference to preferred embodiments, workers skilled in the art will recognize that changes may be made in form and detail without departing from the spirit and scope of the invention.

The invention claimed is:

1. A method of administering reimbursement for services furnished by providers to individuals, the method comprising:
    storing, in a dynamic cost-sharing database, a fee schedule specifying an administrator-determined amount an administrator will reimburse a provider after the provider provides a specified service;
    storing, in the dynamic cost-sharing database, a provider-determined cost-share level that an individual must pay to the provider to receive the specified service, where the cost-share level is based upon cost-share selection data entered by the provider, is alterable at any time by and only by the provider to change total reimbursement to the provider, and is independent of premium costs paid by the individual;
    receiving inputs about specified services and provider criteria from the individual;
    determining current provider cost-share levels based on the stored provider-determined cost-share level and alterations made by the provider to the cost-share level;
    transmitting information from which the individual may select a provider based upon inputs from the individual and database information including the current provider cost-share levels stored in the dynamic cost-sharing database; and
    receiving a provider selection from the individual for specified services, wherein the individual can select any provider in the database at any time and receive the specified service by paying the provider-determined cost-share level in effect when the specified service is provided, and wherein premium costs paid by the individual are independent of the provider selection.

2. The method of claim 1 wherein the cost-share level for specified services varies between providers and between different types of services from the same provider.

3. The method of claim 1 wherein receiving inputs comprises:
    receiving information regarding a condition requiring a treatment plan from an individual;
    receiving information regarding elements of care required for the treatment plan from the individual;
    receiving information regarding provider selection criteria for each element of care from the individual;
    receiving information regarding provider cost-sharing level criteria for each element of care from the individual.

4. The method of claim 3 wherein transmitting information from which the individual may select a provider further comprises:
    transmitting a cost comparison between the selected treatment plan and the treatment plan using other providers.

5. The method of claim 3 wherein transmitting information from which the individual may select a provider further comprises:
    transmitting comparative information about practice characteristics of various providers.

6. The method of claim 1 and further comprising:
    transmitting cost-share levels of peers, at a provider's request, to inform a competitive cost-share level determination.

7. The method of claim 1 and further comprising:
    storing additional information regarding practice characteristics based on receiving such information from providers.

8. The method of claim 1 and further comprising:
    receiving, from a provider, a request for reimbursement; and
    transmitting information for reimbursement to the provider.

9. The method of claim 1 and further comprising:
    receiving, from an individual or provider, information regarding cost-share charges;
    debiting an amount equal to the cost-share from the individual's account; and
    transmitting information regarding payment of cost-share to a provider.

10. A method of administering healthcare using a dynamic cost-sharing database, the method comprising:
    storing a fee schedule, wherein the fee schedule specifies an administrator-determined amount that will be reimbursed to a provider after the provider provides a service;
    storing a provider's preselected cost-share levels for services and practice characteristics, wherein the preselected cost-share levels are independent of premium costs paid by an individual and alterable at any time by and only by the provider to change total reimbursement to the provider;
    receiving inputs from the individual relating to a specified service, cost-share levels and practice characteristics;
    determining current cost-share levels based on the stored preselected cost-share level and alterations made by the provider to the cost-share level;

transmitting information including the current cost-share levels stored in the dynamic cost-sharing database for selecting a provider based on the individual's inputs;

receiving a provider selection from the individual for the specified service, wherein the individual can select any provider in the database at any time and receive the specified service by paying the provider's preselected cost-share level for the specified service in effect when the specified service is provided, and wherein premium costs paid by the individual are independent of the provider selection;

receiving a request for reimbursement from the provider after the specified service has been provided to the individual; and reimbursing the provider based on the stored fee schedule.

11. The method of claim 10 and further comprising:
receiving and storing information regarding cost-shares paid by individuals to providers; and
tracking, for each individual, total cost-share amounts paid.

12. The method of claim 10 and further comprising:
providing an economic analysis of cost-share selections, based on the fee schedule and provider inputs, for selecting cost-share levels for specific services.

13. The method of claim 10 and further comprising:
debiting the cost-share from an individual's account; and
transmitting information to the individual reconciling the account.

14. The method of claim 10 wherein the dynamic cost-sharing database includes a provider information database, an individual information database, and an administrator information database.

15. A method of administering delivery of healthcare services using a dynamic cost-sharing database for reimbursement of single transactions between a healthcare provider and an individual, the method comprising:
receiving and storing a fee schedule specifying an administrator-determined amount a healthcare provider is reimbursed after providing a single transaction of healthcare services;
storing cost-share levels for each transaction based on cost-share selection data received from the healthcare provider, wherein the cost-share levels selected by the healthcare provider are independent of premium costs paid by the individual and alterable at any time by and only by the healthcare provider to change total reimbursement to the healthcare provider;
receiving inputs from the individual for a single transaction and provider criteria;
determining current cost-share levels based on the stored healthcare provider-selected cost-share level and alterations made by the healthcare provider to the cost-share level; and
transmitting information to the individual including the current cost-share levels stored in the dynamic cost-sharing database for selecting a provider based on the individual's inputs and database information, wherein the individual can select any provider in the database at any time and receive a healthcare service by paying the cost-share level selected by the healthcare provider and in effect when the healthcare service is provided, and wherein premium costs paid by the individual are independent of the selection of a provider.

16. The method of claim 15 and further comprising:
receiving, from the provider selected, a request for reimbursement; and
reimbursing the provider based on the stored fee schedule.

17. The method of claim 15 and further comprising:
receiving, from the individual, information regarding a copayment charge;
debiting the copayment amount from the individual's money account; and
crediting the copayment amount to the provider's money account.

18. A method of administering reimbursement for healthcare services using a computer network which includes healthcare administrator terminals, provider terminals, and individual terminals, the method comprising:
storing a fee schedule specifying an administrator-determined amount an administrator will reimburse a provider after providing a healthcare service;
receiving provider-selected cost-sharing for healthcare services and practice characteristics information from a provider terminal, wherein the cost-sharing selected by the provider is independent of premium costs paid by an individual and alterable at any time by and only by the provider to change total reimbursement to the provider;
storing the cost-share and practice characteristics information in a dynamic cost-sharing database;
receiving healthcare requirements and provider selection criteria from an individual terminal;
determining current cost-sharing based on the stored provider-selected cost-sharing and alterations made by the provider to the cost-sharing;
transmitting results of a search of the dynamic cost-sharing database based on the healthcare requirements provider selection criteria to the individual terminal including the current provider cost-share levels stored in the dynamic cost-sharing database; and
receiving a provider selection from the individual, wherein the individual can select any provider in the database at any time and receive a healthcare service by paying the provider-selected cost-sharing for that healthcare service in effect when the healthcare service is provided, and wherein premium costs paid by the individual are independent of the provider selection.

19. The method of claim 18 and further comprising:
receiving proposed cost-share information from the provider terminal;
performing an economic analysis based on the information; and
transmitting results to the provider terminal.

20. The method of claim 18 and further comprising:
receiving a fee schedule from a healthcare administrator terminal; and
storing the fee schedule in a dynamic cost-sharing database.

21. The method of claim 20 and further comprising:
receiving, from a selected provider, a request for reimbursement; and
reimbursing the provider based on the stored fee schedule.

22. The method of claim 18 wherein the provider terminal and individual terminal includes customer service representatives acting on behalf of a provider or individual.

23. A method of conducting an auction of services over a computer network in an insured environment, the method comprising:
storing an insurer's reimbursement schedule for services provided to a plan's members in a dynamic cost-sharing database, wherein the reimbursement schedule specifies an administrator-selected amount that will be reimbursed to a provider after a service is provided;
storing provider practice characteristics and a provider-selected individual cost-share amount that members must pay to the provider at a time of service in the database, wherein the cost-share amount selected by the provider is independent of premium costs paid by members and alterable at any time by and only by the provider to change total reimbursement to the provider;

receiving provider selection criteria from a member;

determining a current cost-share amount based on the stored provider-selected cost-share amount and alterations made by the provider to the cost-share amount; and transmitting information including the current cost-share amount stored in the dynamic cost-sharing database;

for selecting a provider based on the provider selection criteria and information stored in the database, wherein the member can select any provider in the database at any time and receive a service by paying the provider-selected cost-share amount for that service in effect when the service is provided, and wherein premium costs paid by the member are independent of the selection of a provider by the member.

24. The method of claim 23 and further comprising:

storing costs for services furnished by providers not within the plan.

25. The method of claim 23 and further comprising:

transmitting an economic comparison of the amount of cost-share between providers.

26. A method of maintaining a healthcare database, the method comprising:

storing database information provided by multiple healthcare providers and an administrator, the database information including, for each provider, a provider-selected cost-sharing level for each specified service performed by the provider and provider practice characteristics, a fee schedule specifying an administrator-selected amount the administrator will reimburse a provider for each specified service, and a premium cost for an individual, wherein the cost-sharing level selected by the provider for each specified service is independent of the individual's premium cost and alterable at any time by and only by the provider to change total reimbursement to the provider;

receiving inputs from the individual regarding healthcare requirements and provider selection criteria;

determining a current cost-sharing level based on the stored provider-selected cost-sharing level and alterations made by the provider to the cost-sharing level; and transmitting information to the individual regarding search results based on the individual's inputs and stored database information including the current cost-sharing level stored in the dynamic cost-sharing database;

wherein the premium cost paid by the individual is independent of the individual's selection of a provider based on the search results, and wherein the individual can select any provider in the database at any time and receive a specified service by paying the provider-selected cost-sharing level for the specified service in effect when the specified service is provided.

27. The method of claim 26 and further comprising:

receiving information regarding a provider-selected cost-sharing level charged by a provider;

transmitting information to debit an individual's money account an amount equal to the cost-sharing level; and transmitting information to credit the provider's money account the amount of the cost-sharing level.

28. The method of claim 26 and further comprising:

storing a fee schedule set by a healthcare plan to reimburse providers for services.

29. The method of claim 28 and further comprising:

receiving a reimbursement request from a provider; and transmitting information regarding the reimbursement to the provider.

30. A method of administering reimbursement for a service, the method comprising:

storing, in a dynamic cost-sharing database, a fee schedule specifying a reimbursement amount an administrator will pay a provider for providing a service, wherein the reimbursement amount is alterable only by the administrator;

storing, in the dynamic cost-sharing database, a cost-share level specifying an amount an individual must pay to the provider to receive the service, wherein the cost-share level is alterable at any time by and only by the provider to change total reimbursement to the provider;

receiving an input for the service from the individual;

determining a current cost-share level based on alterations made by the provider to the cost-share level;

transmitting provider and cost-share level information to the individual based upon the input received from the individual including the provider cost-share level stored in the dynamic cost-sharing database; and receiving a provider selection for the service from the individual, wherein the individual can select any provider at any time and receive the service by paying the cost-share level specified by the provider and in effect when the service is provided, and wherein premium costs paid by the individual are independent of the provider selection.

* * * * *

UNITED STATES PATENT AND TRADEMARK OFFICE
CERTIFICATE OF CORRECTION

| | | |
|---|---|---|
| PATENT NO. | : 7,769,606 B2 | Page 1 of 1 |
| APPLICATION NO. | : 10/187424 | |
| DATED | : August 3, 2010 | |
| INVENTOR(S) | : H. Keith Boone et al. | |

It is certified that error appears in the above-identified patent and that said Letters Patent is hereby corrected as shown below:

Col. 16, Line 29
   Insert --and-- before provider.

Col. 16, Line 31
   "share levels" should be changed to --sharing--.

Signed and Sealed this
Fifth Day of July, 2011

David J. Kappos
*Director of the United States Patent and Trademark Office*